United States Patent
Smilowitz et al.

(10) Patent No.: US 9,869,644 B2
(45) Date of Patent: Jan. 16, 2018

(54) ULTRAFAST TABLE-TOP DYNAMIC RADIOGRAPHY OF SPONTANEOUS OR STIMULATED EVENTS

(71) Applicant: Los Alamos National Security, LLC, Los Alamos, NM (US)

(72) Inventors: Laura Smilowitz, Los Alamos, NM (US); Bryan Henson, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 49 days.

(21) Appl. No.: 14/937,706

(22) Filed: Nov. 10, 2015

(65) Prior Publication Data
US 2016/0313262 A1    Oct. 27, 2016

Related U.S. Application Data

(60) Provisional application No. 62/152,028, filed on Apr. 23, 2015.

(51) Int. Cl.
| | |
|---|---|
| *G01N 23/222* | (2006.01) |
| *G01N 23/04* | (2006.01) |
| *G01N 33/22* | (2006.01) |
| *H01J 35/04* | (2006.01) |
| *H05G 1/62* | (2006.01) |
| *H05G 1/08* | (2006.01) |

(52) U.S. Cl.
CPC ............ *G01N 23/043* (2013.01); *G01N 23/04* (2013.01); *G01N 33/227* (2013.01); *H01J 35/045* (2013.01); *H05G 1/085* (2013.01); *H05G 1/62* (2013.01)

(58) Field of Classification Search
CPC ......... A61B 6/548; A61B 6/467; A61B 6/544; G01N 23/046; G01N 2223/1016; G01N 24/085; H05G 1/56; H05G 1/58; H05G 1/30; H05G 1/62
USPC ............................ 378/114, 95, 94, 110, 112
See application file for complete search history.

(56) References Cited

U.S. PATENT DOCUMENTS

| | | | | |
|---|---|---|---|---|
| 4,387,722 A | * | 6/1983 | Kearns ............... | A61B 5/02455 378/95 |
| 2013/0077756 A1 | * | 3/2013 | Saar ....................... | G01S 13/88 378/98.12 |

OTHER PUBLICATIONS

Bernert et al., "In situ observation of self-propagating high temperature syntheses of $Ta_5Si_3$, $Ti_5Si_3$ and $TiB_2$ by proton and X-ray radiography," *Solid State Sciences*, vol. 22, pp. 33-42 (May 2013).

(Continued)

*Primary Examiner* — Don Wong
(74) *Attorney, Agent, or Firm* — Klarquist Sparkman, LLP

(57) ABSTRACT

Disclosed herein are representative embodiments of methods, apparatus, and systems for performing radiography. For example, certain embodiments concern X-ray radiography of spontaneous events. Particular embodiments of the disclosed technology provide continuous high-speed x-ray imaging of spontaneous dynamic events, such as explosions, reaction-front propagation, and even material failure. Further, in certain embodiments, x-ray activation and data collection activation are triggered by the object itself that is under observation (e.g., triggered by a change of state detected by one or more sensors monitoring the object itself).

18 Claims, 19 Drawing Sheets

(56) References Cited

OTHER PUBLICATIONS

Chidester et al., "On the violence of thermal explosion in solid explosives," *Combustion and Flame*, vol. 110, pp. 264-280 (Jul. 1997).

Garcia et al., "Pressure Wave Measurements Resulting from Thermal Cook-Off of the HMX Based High Explosive LX-04," *AIP Conf. Proc.*, vol. 706, pp. 947-950 (Jul. 2003).

Garcia et al., "Thermal Cook-Off Experiments of the HMX Based High Explosive LX-04 to characterize Violence with Varying Confinement," *AIP Conf. Proc.*, vol. 845, pp. 1061-1064 (Aug. 2005).

Henson et al., "The β—δ phase transition in the energetic nitramine octahydro-1,3,5,7-tetranitro-1,3,5,7-tetrazocine: Thermodynamics," *Journal of Chemical Physics*, vol. 117, pp. 3780-3788 (2002).

Kaneshige et al., "Development of Scalable Cook-Off Models Using Real-Time in Situ Measurements," *AIP Conf. Proc.*, vol. 706, pp. 351-354 (Jul. 2003).

Rodriguez et al., "Coherent pulse interrogation system for fiber Bragg grating sensing of strain and pressure in dynamic extremes of materials," *Optics Express*, vol. 23, No. 11, 15 pp. (Jun. 2015).

Rodriguez et al., "Insight into fiber Bragg sensor response at 100 MHz interrogation rates under various dynamic loading conditions," *Proc. SPIE*, vol. 9480, 15 pp. (May 2015).

Smilowitz et al., "Direct Observation of the Phenomenology of a Solid Thermal Explosion Using Time-Resolved Proton Radiography," *Physical Review Letters*, vol. 100, 4 pp. (Jun. 2008).

Smilowitz et al., "Dynamic X-ray of Thermal Explosions," Los Alamos National Laboratory LA-UR-15-22224, 3 pp. (Mar. 2015).

Smilowitz et al., "Fast Internal Temperature Measurements in PBX9501 Thermal Explosions," *AIP Conf. Proc.*, vol. 845, pp. 1211-1214 (Aug. 2005).

Smilowitz et al., "Following Reaction Progress from Thermal Decomposition to Ignition and Internal Burning," *In'tl Detonation Symp.*, 9 pp. (Jul. 2014).

Smilowitz et al., "The Evolution of a Thermal Explosion-Spatial and Temperature Profiles Internal to a PBX9501 Thermal Explosion," *Thirteenth Int'l Symp. on Detonation*, pp. 1026-1034 (Jul. 2006).

Smilowitz et al., "The evolution of solid density within a thermal explostion. I. Proton radiography of pre-ignition expansion, material motion, and chemical decomposition," *Journal of Applied Physics*, vol. 111, 8 pp. (May 2012).

Smilowitz et al., "The evolution of solid density within a thermal explosion II. Dynamic proton radiography of cracking and solid consumption by burning," *Journal of Applied Physics*, vol. 111, 12 pp. (May 2012).

Smilowitz et al., "The β—δ phase transition in the energetic nitramine-octahydro-1,3,5,7-tetranitro-1,3,5,7-tetrazocine: Kinetics," *Journal of Chemical Physics*, vol. 117, pp. 3789-3798 (2002).

Smilowitz et al., "Thermal decomposition of energetic materials viewed via dynamic x-ray radiography," *Applied Physics Letters*, vol. 104, 4 pp. (Jan. 2014).

Smilowitz et al., "Thermal Explosions: Sub-sonic Deflagration in PBX 9501," Los Alamos National Laboratory LA-UR-11-07094, 23 pp. (Jan. 2012).

Smilowitz et al., "X-Ray Radiographic Studies of the Deflagration to Detonation Transition in Porous Beds of Explosives," *Int'l Colloquium on the Dynamics of Explosions and Reactive Systems*, 5 pp. (Aug. 2015).

Smilowitz et al., "X-ray transmission movies of spontaneous dynamic events," *Review of Scientific Instruments*, vol. 85, 5 pp. (Nov. 2014).

\* cited by examiner

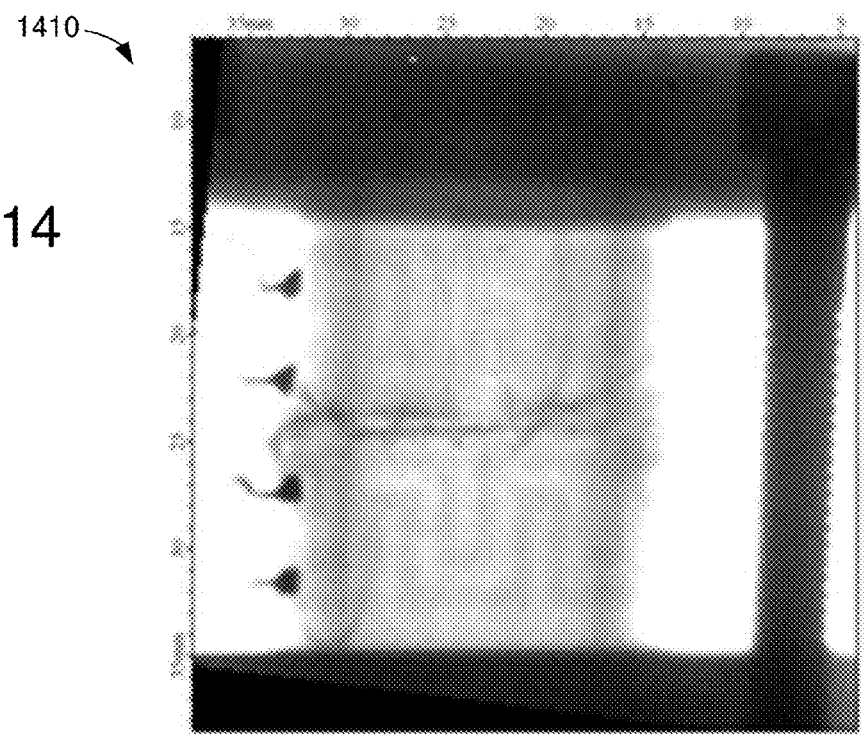
Figure 14
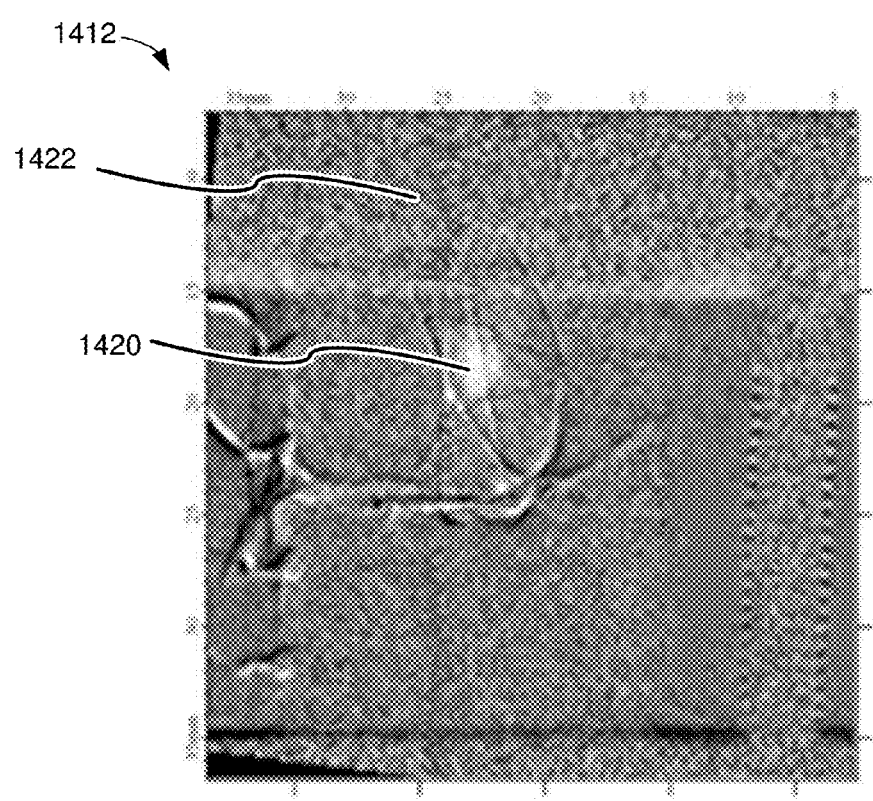

ULTRAFAST TABLE-TOP DYNAMIC RADIOGRAPHY OF SPONTANEOUS OR STIMULATED EVENTS

CROSS REFERENCE TO RELATED APPLICATIONS

This application claims the benefit of U.S. Provisional Patent Application No. 62/152,028, filed on Apr. 23, 2015, and entitled "ULTRAFAST TABLE-TOP DYNAMIC RADIOGRAPHY OF SPONTANEOUS EVENTS", which is hereby incorporated herein by reference in its entirety.

ACKNOWLEDGEMENT OF GOVERNMENT SUPPORT

This invention was made with government support under Contract No. DE-AC52-06NA25396 awarded by the U.S. Department of Energy. The government has certain rights in the invention.

FIELD

This application relates to the field of radiography. For example, certain embodiments concern X-ray radiography of spontaneous events.

SUMMARY

Disclosed herein are representative embodiments of methods, apparatus, and systems for performing radiography. For example, certain embodiments concern X-ray radiography of spontaneous events. The disclosed methods, apparatus, and systems should not be construed as limiting in any way. Instead, the present disclosure is directed toward all novel and/or nonobvious features and aspects of the various disclosed embodiments, alone or in various combinations and subcombinations with one another.

Embodiments of the disclosed technology (sometimes referred to as the LARS (Lab-scale Asynchronous Radiographic System)) comprise a benchtop system capable of time-resolved x-ray imaging of spontaneous or stimulated dynamic events. Certain example embodiments of LARS produce continuous x-ray movies of complex objects with a variable field of view (e.g., as great as 200 mm, although larger fields of view could be obtained with a tradeoff of spatial resolution and temporal resolution), durations that range from sub-microseconds to days (e.g., microseconds to seconds), and a spatial resolution of 300 microns or better.

With its relatively small size and low cost, embodiments of LARS make x-ray radiography available at the bench scale. Further, certain embodiments of LARS can provide continuous high-speed x-ray imaging of spontaneous dynamic events, such as explosions, reaction-front propagation, and even material failure. Because LARS embodiments enable the everyday evaluation of these events in individual labs, the system greatly broadens the range of applications for x-ray radiography. Such a capability is a game changer in fields as diverse as dynamic chemical synthesis, material failure, and explosives physics. Consequently, using embodiments of the disclosed technology, it is possible for dynamic radiography to become a relatively inexpensive, small-scale standard diagnostic tool.

Embodiments of the disclosed technology can be configured to image spontaneous or stimulated dynamic events. For example, one example radiographic imaging method disclosed herein comprises automatically triggering generation of x-rays and image data collection for transmission images resulting from the x-rays using one or more measurements of an object being imaged by the x-rays. The measurements can, for example, indicate a change of state in the object. In some implementations, the object is an explosive material and the measurements indicate that the object has entered a state of explosion. In other implementations, the object is a material being strained and the measurements indicate that the object has entered a state of material failure. In further implementations, the object is a material experiencing an exothermic reaction and the measurements indicate that the object has entered a state of exothermic reaction. The measurements can be obtained from one or more sensors embedded into the object, sensors in contact with a surface of the object, and/or sensors not in contact with the object but configured to directly sense or detect a characteristic of the object. In some implementations, the generation of x-rays is performed by a gridded x-ray source, and image data collection is performed by a video camera. In such cases, the x-ray source and the video camera operate as part of an x-ray transmission imaging system in which x-rays interrogate the object and are detected by a scintillator, the scintillator producing light signals captured and recorded by the camera in the form of continuous video data comprising multiple consecutive frames.

Another example radiographic imaging method disclosed herein comprises placing an x-ray source into an armed state in which elements of the x-ray source are operative and ready for x-ray generation but no x-rays are generated; and triggering the x-ray source to transition into an active x-ray generation state using a signal that originates from an event occurring in an object to be imaged using the generated x-rays from the x-ray source. The signal can be produced using hardware logic components that are coupled to one or more sensors configured to detect occurrence of the event in the object. At least one of the one or more sensors can be in contact with the object. In some implementations, the object to be imaged is an explosive material and the event is an onset of an explosion of the explosive material during a period of thermal runaway experienced by the explosive material. In other implementations, the object to be imaged is a material being strained and the event is an onset of a material failure of the material being strained. In further implementations, the object to be imaged is a material experiencing an exothermic reaction and the event is an onset of the exothermic reaction. In some implementations, activation of a video capture system configured to produce x-ray transmission images of the object is triggered in response to the generated x-rays from the x-ray source. For example, the video capture system can also be activated by the signal that is generated from the event occurring in the object to be imaged.

Another embodiment of the disclosed technology is a system, comprising: an x-ray source, the x-ray source comprising a gridded x-ray tube; a scintillator positioned to receive x-rays generated by the x-ray source; a video capture system configured and arranged to, when activated, capture and store image data produced by the scintillator for multiple consecutive frames; and an object to be x-ray imaged using the x-ray source, the scintillator, and the video capture system, the object being located between the x-ray source and the scintillator. The system can be sized and configured to fit on a table top. The system can further comprise a containment vessel located between the x-ray source and the scintillator, the containment vessel being configured to hold the object to be x-ray imaged. In some embodiments, the system further comprises a trigger mechanism for providing a trigger signal that causes the x-ray source to begin generating x-rays. In such embodiments, the x-ray source can be configured to transition from an armed state into an x-ray generation state upon receipt of the trigger signal, the armed state being a state in which a cathode and an anode of the x-ray source are active but electrons are deflected from interaction with the anode through a voltage applied to the gridded x-ray tube. For instance, the trigger signal can cause a grid voltage in the gridded x-ray tube to change into a state that permits electrons from a cathode in the x-ray source to strike an anode in the x-ray source, thereby generating x-rays. In some implementations, the trigger mechanism comprises: one or more sensors configured to sense a characteristic of the object to be imaged; and one or more hardware logic components (e.g., dedicated hardware logic components or logic components of an oscilloscope) in communication with the one or more sensors and configured to generate the trigger signal when the one or more sensors produce one or more signals indicating that a trigger threshold has been reached. In some implementations, the one or more sensors include one or more of a sensor located within the object; a sensor positioned in contact with a surface of the object; and/or a sensor positioned proximate to but not in contact with the object. Further, the one or more sensors include one or more of a temperature sensor, light sensor, strain sensor, pressure sensor, or sound sensor. In some implementations, the x-ray source is adapted from a fluoroscopy x-ray source.

Another embodiment of the disclosed technology is a system, comprising: an x-ray source; a scintillator positioned to receive x-rays generated by the x-ray source; a video capture system configured and arranged to, when activated, capture and store image data produced by the scintillator for multiple consecutive image frames; an object to be x-ray imaged using the x-ray source, the scintillator, and the video capture system, the object being located between the x-ray source and the scintillator; and a trigger mechanism for providing a trigger signal that causes the x-ray source to begin generating x-rays, the trigger mechanism comprising one or more sensors configured to sense a characteristic of the object to be imaged, and one or more hardware logic components in communication with the one or more sensors and configured to automatically generate the trigger signal when the one or more sensors produce one or more signals indicating that a trigger threshold has been reached. The system can be sized and configured to fit on a table top. The system can further comprise a containment vessel located between the x-ray source and the scintillator, the containment vessel being configured to hold the object to be x-ray imaged. In some implementations, the one or more sensors include one or more of: (a) a sensor located within the object; (b) a sensor positioned in contact with a surface of the object; or (c) a sensor positioned proximate to but not in contact with the object. The one or more sensors include one or more of a temperature sensor, light sensor, strain sensor, pressure sensor, or sound sensor.

Another embodiment of the disclosed technology is a system, comprising: an x-ray source; a video capture system having a direct detection x-ray camera, the video capture system being configured and arranged to, when activated, capture and store image data produced by x-ray detected by the direct detection x-ray camera for multiple consecutive image frames; an object to be x-ray imaged using the x-ray source and the video capture system, the object being located between the x-ray source and the video capture system; and a trigger mechanism for providing a trigger signal that causes the x-ray source to begin generating x-rays, the trigger mechanism comprising one or more sensors configured to sense a characteristic of the object to be imaged, and one or more hardware logic components in communication with the one or more sensors and configured to automatically generate the trigger signal when the one or more sensors produce one or more signals indicating that a trigger threshold has been reached. The system can further comprise a containment vessel located between the x-ray source and the scintillator, the containment vessel being configured to hold the object to be x-ray imaged. In some implementations, the one or more sensors include one or more of: a sensor located within the object; a sensor positioned in contact with a surface of the object; or a sensor positioned proximate to but not in contact with the object. The one or more sensors include one or more of a temperature sensor, light sensor, strain sensor, pressure sensor, or sound sensor.

Another embodiment of the disclosed technology is a multi-axis radiography system. For example, such a system can comprise: a first x-ray source; a first scintillator positioned to receive x-rays generated by the x-ray source; a first video capture system configured and arranged to, when activated, capture and store image data produced by the first scintillator for multiple consecutive frames; a second x-ray source; a second scintillator positioned to receive x-rays generated by the second x-ray source; a second video capture system configured and arranged to, when activated, capture and store image data produced by the scintillator for multiple consecutive frames; and an object to be imaged being located between the first x-ray source and the first scintillator, and also being located between the second x-ray and the second scintillator, the first x-ray source, the first scintillator, and the first video capture system being arranged to image the object along a first axis, the second x-ray source, the second scintillator, and the second video capture system being arranged to image the object along a second axis. In some implementations, the first x-ray source is a pulsed x-ray with at least 60 kVp, and the second x-ray source is a continuous x-ray source. In some implementations, the first video capture system is configured to image the object with faster time resolution than the second video capture system. In further implementations, the first video capture system is configured to image the object over a shorter duration than the second video capture system. In some implementations, the system further comprises a trigger mechanism for providing a trigger signal that causes the first x-ray source to begin generating x-rays, the trigger mechanism comprising one or more sensors configured to sense a characteristic of the object to be imaged, and one or more hardware logic components in communication with the one or more sensors and configured to automatically generate the trigger signal when the one or more sensors produce one or more signals indicating that a trigger threshold has been reached. The trigger mechanism can be configured to trigger the first x-ray source but not the second x-ray source. This can also be configured with multiple identical x-ray systems to get multiple angular views with the same or different time and spatial resolution.

The foregoing and other objects, features, and advantages of the invention will become more apparent from the following detailed description, which proceeds with reference to the accompanying figures.

BRIEF DESCRIPTION OF THE DRAWINGS

FIG. 14 shows the direct transmission image and change in transmission image of a thermal explosion experiment discussed herein.

DETAILED DESCRIPTION

I. General Considerations

Figure 1:
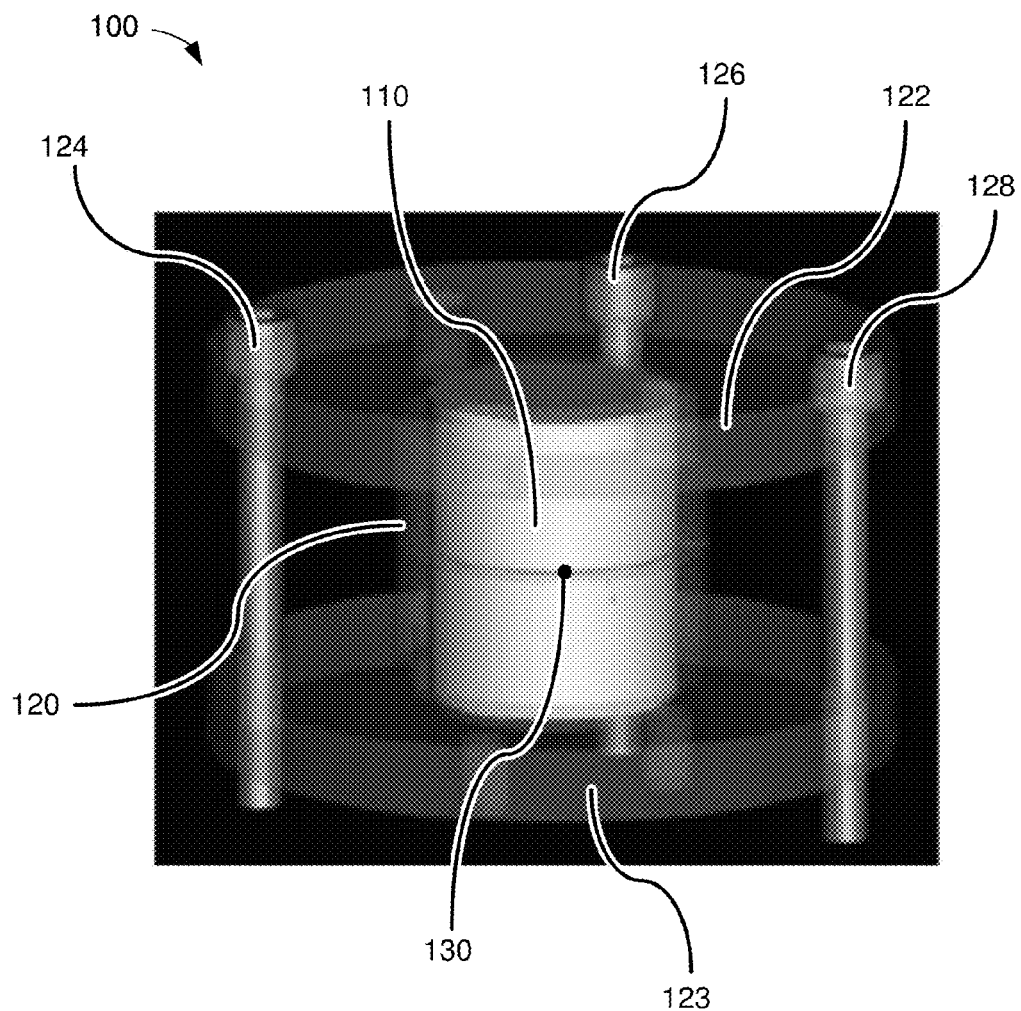
FIG. 1 is a schematic diagram of an explosive article studied in an example system discussed herein.

Disclosed below are representative embodiments of methods, apparatus, and systems for performing radiography. For example, certain embodiments concern X-ray radiography of spontaneous or stimulated events. The disclosed methods, apparatus, and systems should not be construed as limiting in any way. Instead, the present disclosure is directed toward all novel and nonobvious features and aspects of the various disclosed embodiments, alone or in various combinations and subcombinations with one another. Furthermore, any feature or aspect of the disclosed embodiments can be used in various combinations and subcombinations with one another. For example, one or more method acts or features from one embodiment can be used with one or more method acts or features from another embodiment and vice versa. The disclosed methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "determine," "provide," and "optimize," to describe the disclosed methods. These terms are high-level abstractions of the actual operations that are performed. The actual operations that correspond to these terms may vary depending on the particular implementation and are readily discernible by one of ordinary skill in the art. Furthermore, in general, and as used herein, the term "optimal" describes a solution that satisfies some set of criteria better than other solutions according to some parameterization or modeling, which may or may not be optimal in absolute terms depending on circumstances, and the term "optimize" or "optimization" is used to indicate the process of finding such a solution. Additionally, as used herein, the term "and/or" means any one item or combination of any items in the phrase.

II. Overview of Disclosed Technology

Described herein are methods, systems, and apparatus that can be used to perform radiography of spontaneous dynamic events. Certain embodiments comprise a table-top radiographic system that can be used to collect continuous x-ray movies of spontaneous or stimulated dynamic events with ultrafast time resolution (e.g., sub-microsecond or microsecond time resolution). In some implementations, the system is small enough to be used on a benchtop in a lab. The system can be used to image a variety of spontaneous or stimulated events—including without limitation thermal explosions, reaction propagation, material failure, ballistics, etc., with time resolution of microseconds or better. Further, in certain embodiments, the imaging is triggered by the event itself.

Figure 6:
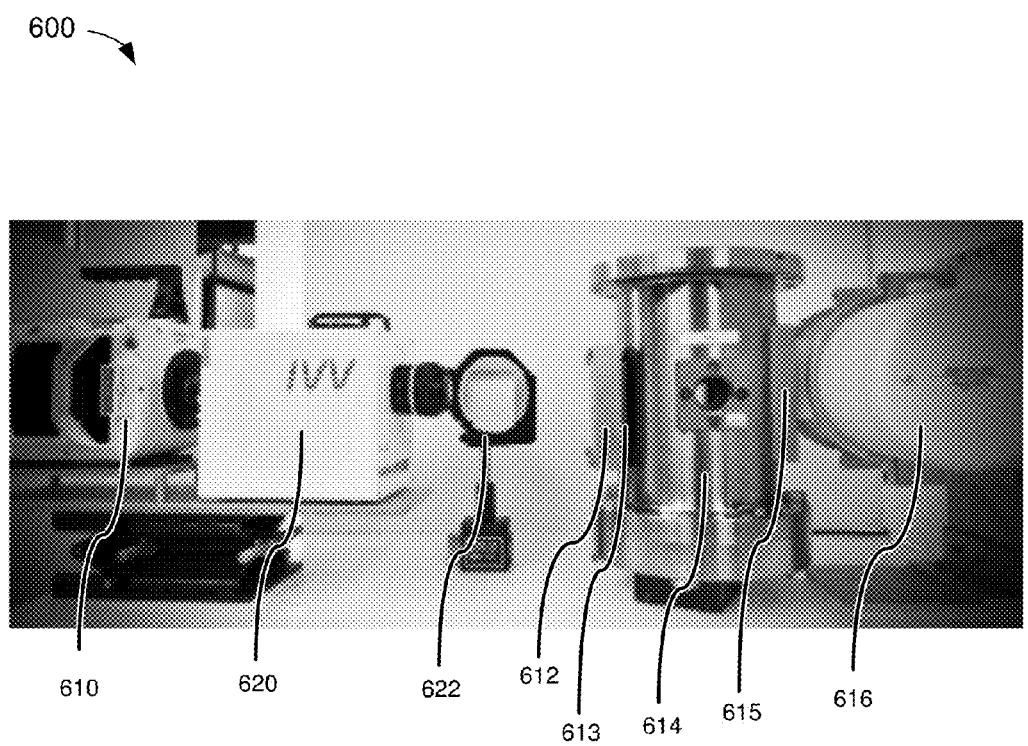
FIG. 6 is an image of an actual example table-top spontaneous dynamic x-ray radiography system in accordance with the disclosed technology.

FIG. 6 is an image 600 of an example embodiment of a Lab-scale Asynchronous Radiographic System (LARS) according to the disclosed technology. In the illustrated embodiment, LARS comprises a camera 610, a scintillator 612, a vessel 614 used for thermal-explosion studies, and an x-ray tube 616. In some embodiments, the scintillator 612 is omitted and the camera itself performs a direct conversion (e.g., a direct x-ray camera). In particular embodiments, the vessel 614 is configured to include a window 615 that allows for the x-ray beam from the x-ray tube 616 to interrogate an object (not visible) held within the vessel 614. That window can be made of any low atomic number material transparent to x-rays, such as carbon fiber, aluminum, or a combination of a carbon fiber plate and an aluminum plate. Windows transparent to visible light, such as lexan, can also be used. Further, the scintillator 612 is located next to or adjacent another window of the vessel opposite of the x-ray-source-side window that allows the scintillator to receive x-rays transmitted through the object being imaged. That window can be made of any low atomic number material transparent to x-rays, such as carbon fiber, aluminum, or a combination of a carbon fiber plate and an aluminum plate. Windows transparent to visible light, such as lexan, can also be used. Also shown in FIG. 6 is an image intensifier 620 and a turning mirror 622. The image intensifier 620 is optionally used with the camera 610 as part of a video capture system (also referred to as the imaging system). The turning mirror 622 is optionally used to redirect the output from scintillator so that the camera 610 (and other components of the video capture system, such as the optional image intensifier 620) can be placed out of the x-ray beam path of the x-ray source.

Particular embodiments of the disclosed radiography system operate using a gridded (or grid controlled) x-ray tube and an imaging system with a cyclic buffer. The gridded or grid controlled x-ray system allows the x-ray tube to be turned on and held in an armed state awaiting a trigger to provide x-rays. Other embodiments do not use a gridded x-ray tube but can be activated relatively quickly (e.g., in response to a trigger signal). The imaging system can use a scintillator to convert x-rays to visible light, or a direct x-ray camera. A high-speed camera with a cyclic memory buffer enables camera triggering at any point during or even after the event occurs. Embodiments of the disclosed system can capture x-ray movies at, for example, up to one million frames per second or higher.

Image rate and duration can be selected for specific applications. Lower repetition rates can be used for slower events, such as viscosity measurement or rocket motor burning. Such low repetition rates enable longer duration imaging (minutes to days or longer).

Particular embodiments of the disclosed technology effectively "miniaturize" a radiographic facility to one that can be built on a benchtop in a lab. It is therefore broadly accessible. Additionally, the use of an x-ray pulse which is long compared to the dynamic event enables continuous ultrafast video monitoring over the entire duration of the event. Still further, the ability to trigger the x-rays on demand enables radiography of spontaneous dynamic events.

One example embodiment of the disclosed technology uses a long pulse x-ray source available from the field of medical radiography/fluoroscopy in addition to a fast, high efficiency scintillator and ultrafast framing camera to enable collection of ultrafast x-ray movies of dynamic events. In particular implementations, the long pulse x-ray has a relatively long duration compared to the event being imaged (e.g., 80 ms or longer (in some cases, longer pulses can be made possible by lowering x-ray flux)); multiple frames of the event are captured (e.g., 100 or more frames, 1000 or more frames, 10,000 or more frames, or 100,000 or more frames); the field of view is relatively large (e.g., 125 mm or larger); x-ray generation can be triggered asynchronously (e.g., can be triggered on demand, such as by the event being imaged itself); the system is configured to fit on a table top (e.g., a laboratory table top or other lab-scale support surface); and/or the system is relatively inexpensive (e.g., about $300,000). Example dimensions of embodiments of the disclosed system include 10 ft.×10 ft. or smaller, 6 ft.×6 ft. or smaller, or 3 ft.×3 ft. or smaller.

As noted, in certain embodiments, the event itself can be used to trigger the start of the x-ray pulse so that spontaneous dynamic events can be captured. Any signal generated by the event (e.g., heat, light, voltage, stress, strain, noise, etc.) can be used to provide the trigger to the x-ray source and camera. Examples of applications demonstrated have been the radiography of thermal explosions and transitions to and from detonations. Further, in some cases, slower events can be captured using multiple pulses spaced out in time or CW (continuous wave) x-ray sources. In some embodiments, multiple systems are used together (e.g., in a multi-axis configuration) to record both longer-term events as well as fast events (e.g., explosive events).

Other advantages that can be realized by embodiments of LARS include one or more of: (a) the capability to capture truly asynchronous events as a result of the system's extremely short time lag between trigger and x-rays; such capability allows LARS to capture events that have previously been difficult (or impossible) to capture, such as abnormal detonator function, thermal explosions, gun systems, and material failure; (b) the capability to perform table-top capture of truly spontaneous dynamic events (e.g., with a system having a size of 10 ft.×10 ft. or smaller, 6 ft.×6 ft. or smaller, or 3 ft.×3 ft. or smaller); and/or (c) the capability to provide continuous illumination over a relatively long period of time (e.g., 80 ms or greater) rather than using only a single short x-ray pulse for a single frame; thus, for instance, embodiments of LARS make it possible to continuously observe and capture video of the entirety of an event rather than capturing a single freeze frame during the event; the resultant multi-frame videos enable scientists to gain a better understanding of complex events.

III. Detailed Description of Embodiments of the Disclosed Technology

In this section, example embodiments of the disclosed radiographic system (e.g., embodiments of LARS) are described in more detail. Embodiments of the disclosed technology include an x-ray radiographic imaging system that allows for continuous x-ray transmission imaging of spontaneous dynamic events. For instance, certain example systems use triggering techniques that enable the continuous imaging of a thermal explosion. In other embodiments, the system is adapted for imaging of stimulated events.

Experimental results from using an embodiment of the disclosed systems are also disclosed. In particular, experimental results from an example system are disclosed in which the system was used to image and analyze a thermal explosions in three plastic bonded formulations of the energetic material octahydro-1,3,5,7-tetranitro-1,3,5,7-tetrazocine (HMX).

A. Introduction

High-energy penetrating radiography allows imaging through opaque objects in fields such as medical imaging and non-destructive testing. Disclosed herein are example embodiments of an x-ray radiography system (sometimes referred to as the Lab-scale Asynchronous Radiographic System (LARS)) that allows continuous x-ray illumination of a dynamic event with the ability to trigger the x-rays from the spontaneous event. The subsections below describe example systems in more detail as well as the use of such a system to image spontaneous thermal explosions, though such application should not be construed as limiting.

Spontaneous thermal explosions have been historically difficult to study due to the evolution of the thermal runaway over the course of minutes, hours, or even days, depending on the specific temperature to which the system is being exposed, with the final dynamic event being spontaneously generated with a duration of tens to hundreds of microseconds. This means that in order to follow the entire material evolution from initial thermal expansion and decomposition through to ignition propagation and case failure, data is desirably collected for time scales ranging over 9 orders of magnitude. Additionally, both the explosive and the confinement are optically opaque, requiring high energy x-rays to penetrate.

Example embodiments of the disclosed x-ray system are capable of producing x-ray transmission movies of spontaneous thermal explosions utilizing x-ray energies that are similar to those used in medical imaging, as the density of secondary organic crystalline explosives is on the order of 2 g/cc, which is similar to bone density. Further, in certain embodiments, the duration of the event is sub-millisecond, meaning the example systems can remain activated for the duration of the thermal explosion event.

Coupling the x-ray source, which is on for a duration of milliseconds, with a scintillator and an imaging system with microsecond or faster time resolution allows for continuous x-ray transmission movies to be captured and spatially resolved dynamic changes in transmission over many rates of change measured.

In order to capture the spontaneous thermal explosion, and in certain embodiments of the disclosed technology, the x-ray system is kept in an armed state from which the onset of x-rays can be generated within microseconds of the event-generated trigger. In order to have sufficient x-ray photon flux to be able to capture images with a reasonable signal-to-noise ratio for imaging, the x-ray source is desirably run with very high kVp and mA. For instance, the kVp is desirably 60 kVp or higher, such as in the range of 60-300 kVp, depending on the object to be imaged; and the x-ray filament current is 500 mA or higher, such as at or near 800 mA. For instance, for the example experiments discussed herein, the combination of object size and opacity with microsecond time-resolution indicated that the working x-ray energy were desirably 60 kVp or higher (e.g., in the 80-100 kVp range) and that the x-ray filament currents were 500 mA or higher (e.g., at or near 800 mA) A 100 kVp, 800 mA system can be implemented using an 80 kW x-ray generator. However, heat dissipation in the x-ray tube anodes at such high flux limits the duration of the x-ray pulse. This means that the x-ray filament cannot be held continuously at 800 mA for the minutes or longer, during which the spontaneous dynamic event is possible, without damaging the x-ray head. In other embodiments, however, the event being imaged may be slower, allowing for millisecond time resolution. In these cases, x-ray filament currents lower than 500 mA can be used, such as x-ray filament currents in the 0.1 mA-500 or 10-500 mA range.

In order to meet the desired behavior of spontaneous triggering as well as the other desired system behaviors, a gridded x-ray tube is used in certain embodiments of the disclosed technology. This allows the x-ray head to be kept in an armed state where the anode is spinning, the filament is heated to generate electron flux, and the accelerating voltage is on. But the grid voltage of the gridded tube can be used to prevent the electrons generated at the cathode from reaching the anode and generating x-rays. The trigger pulse then controls the grid voltage to shut off and allow the high energy electrons to reach the anode and generate x-rays. Other embodiments do not use a gridded x-ray tube but can still be activated quickly, and thus are desirably used in embodiments of the disclosed technology. For example, certain x-ray sources (e.g., certain veterinary x-ray sources, dental x-ray sources, or fluoroscopy x-ray sources) can be activated relatively quickly from a disarmed state to an activated state in which x-rays are being generated. Although such sources are not as fast as a gridded source as described above, they can be used in embodiments of the disclosed technology for applications that allow for slower response times.

B. Example Experimental Method

An example application which beneficially uses embodiments of the disclosed systems is the study of thermal explosions in secondary high explosives (HE). Secondary high explosives are materials that are capable of releasing energy in very short of amounts of time in detonations but only in response to specific stimuli. They are characterized by good stability to stimuli making them safer to handle than more sensitive explosives. Characterizing their response to heat-generating stimuli is desirable in determining their safety envelope. Studies of thermal response of secondary high explosives precipitated the desirability for radiographing thermal explosions, which are inherently spontaneous events. Heating the secondary high explosive to high enough temperature and for long enough duration induces the exothermic chemistry in the explosive that then increases the temperature and accelerates the reactions. This leads to runaways in temperature and reaction rate, which can initiate burning and thermal explosion.

FIG. 1, for instance, shows a schematic 100 of the explosive article studied in an example experiment discussed herein. In particular, a secondary explosive 110 is encased in aluminum (represented schematically in FIG. 1 as an encasing 120 with end caps 122, 123 secured with steel screws 124, 126, 128). The white region in the figure is HE 110, the surrounding light grey is an aluminum case 120, and the dark grey shows the steel screws 124, 126, 128. In this particular example, the experiment was a large 25.4 mm (1") 1:1 aspect ratio experiment. The explosive comprised 2 halves mated at the midplane allowing for diagnostic instrumentation at the center of the explosive. For instance, in the experiments discussed herein, a thermocouple (shown schematically as thermocouple 130) was located at the center of the explosive and used to measure internal temperature of the material. Such a thermocouple can be used to detect that a threshold temperature was reached, thus indicating explosion and, in certain embodiments of the disclosed technology, providing a trigger to activate the x-ray source and image recording at the camera of the radiography system.

Figure 2:
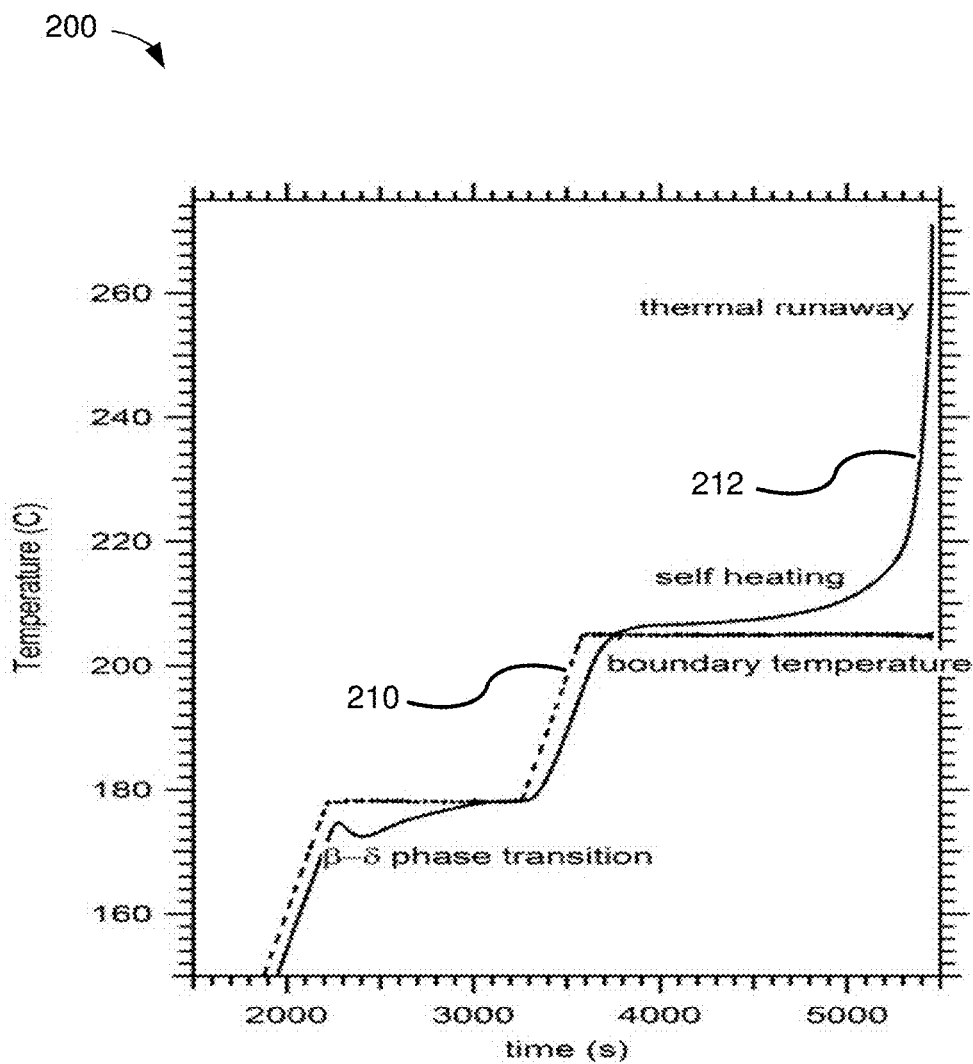
FIG. 2 is a graph showing the internal temperature as a function of time for a typical thermal explosion experiment as can be imaged using embodiments of the system disclosed herein.

FIG. 2 is a graph 200 that shows the internal temperature as a function of time for a typical thermal explosion experiment of the energetic material Formulation PBX 9501 heated to a temperature of over 200° C. For FIG. 2, temperature traces were taken at a boundary of the aluminum case/HE (e.g., using one or more thermocouples) as well as internal to HE during heating to thermal explosion in an HMX based formulation (e.g., using one or more thermocouples located internal to the explosive). Plot 210 shows the temperature at the boundary of the aluminum while plot 212 shows the temperature internal to HE during heating to thermal explosion.

The thermal runaway is seen in plot 212 as the final increase in internal temperatures with the boundary held at 205° C. The evolution of the thermal runaway in this material is reproducible to within minutes or seconds, depending on the ability to accurately control the boundary temperature. The ignition event takes tens of minutes to generate in this material at this temperature but, the propagation of ignition in the thermal explosion takes only microseconds. While time of ignition can be predicted within tens of seconds for an event taking thousands of seconds to generate, it cannot be predicted to within tens of microseconds, which would be necessary in order to capture the final dynamic event (burn propagation) through prediction. This disparity in experimental time scales and the inherently spontaneous nature of this and many phenomena are among the motivations for the modification of grid technologies used to manipulate the current at the anode of the x-ray source and the overall strategy and assembly of example embodiments of the laboratory scale radiography system as disclosed herein. For example, the triggering mechanism used to activate x-ray generation in certain embodiments of the disclosed technology is based on an event detected in the observed object itself. Thus, x-ray activation and imaging is not externally controlled, but internally controlled by the event under observation itself. This system could also be applied to stimulated events with the x-ray activation being provided by the stimulated event itself. For example, an embodiment of the disclosed x-ray radiography system could be configured such that an event is triggered by a detonator and the pulse that triggers the detonator also provides the trigger timing for the x-ray system.

C. Triggering

Figure 4:
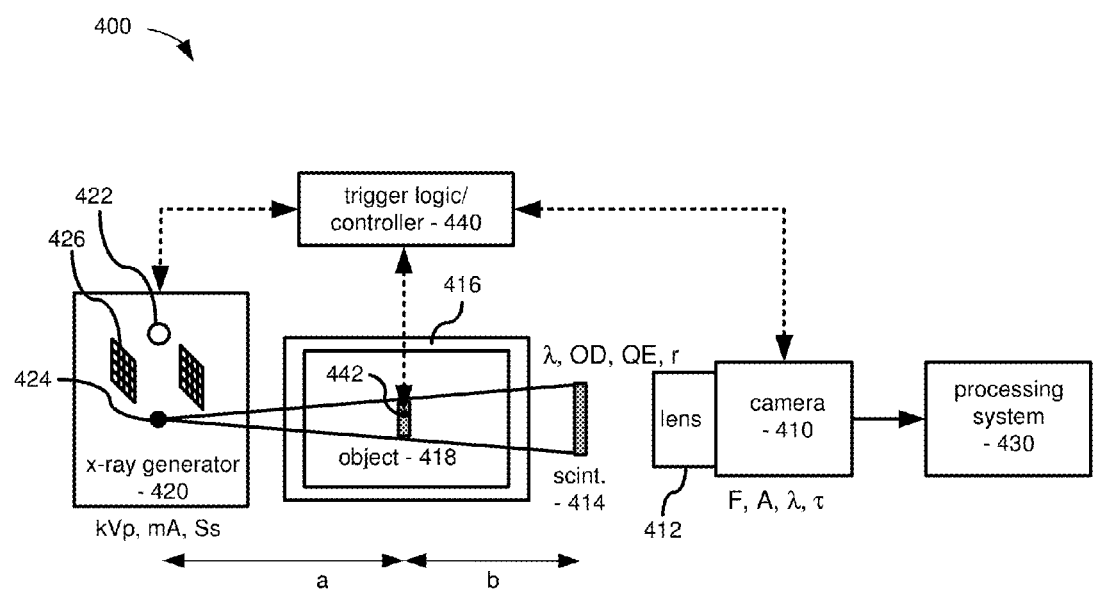
FIG. 4 is a schematic block diagram of an example spontaneous dynamic x-ray radiography system in accordance with the disclosed technology.
Figure 5:
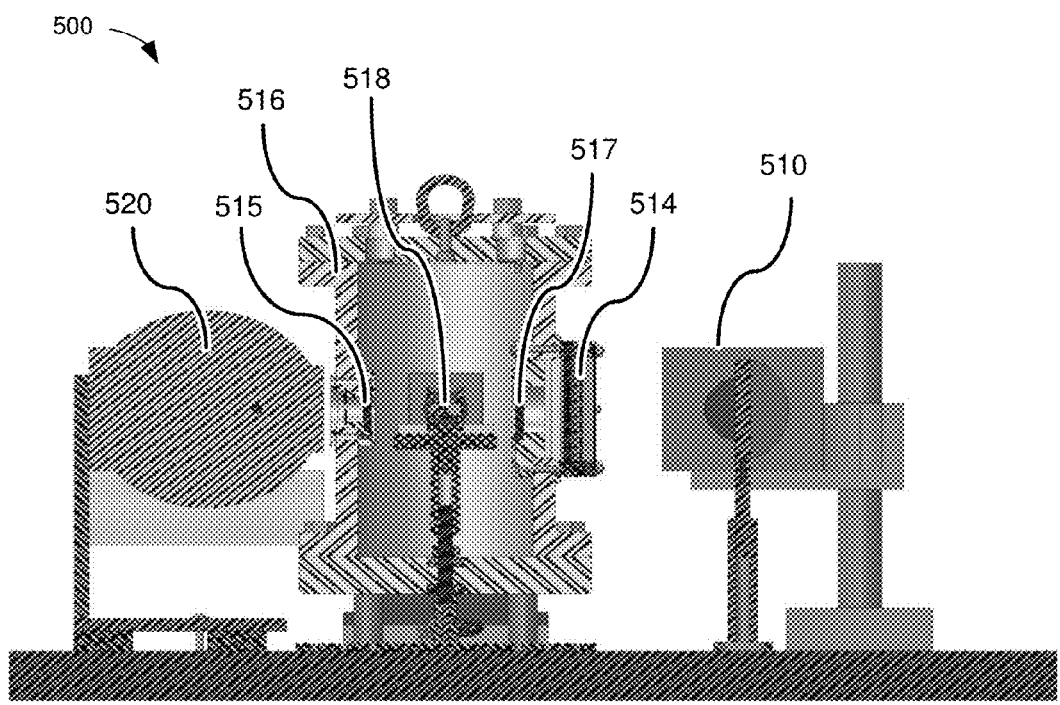
FIG. 5 is another schematic block diagram showing in more detail and in a cross-sectional view an example table-top spontaneous dynamic x-ray radiography system in accordance with the disclosed technology.

This section describes example triggering mechanisms and/or techniques that can be used in embodiments of the disclosed technology (e.g., any embodiment disclosed herein, such as the example configurations shown in FIGS. 4, 5, and 6). The particular mechanisms disclosed, however, should not be construed as limiting, however, as other triggers can also be used with the disclosed technology.

In order to capture spontaneous, dynamic events, (e.g., the final ~100 microsecond spontaneous dynamic event occurring at the end of the several hour long experiment), a signature from early in the event can be used to start (trigger) the x-ray flux and/or also image collection. For instance, a signal indicating the onset of an event to be observed can provide the trigger to activate the x-ray source (e.g., by changing the voltage in the grid of the gridded x-ray tube) and to activate the diagnostic system to begin data acquisition (e.g., by triggering the camera to record or store the received images). With embodiments of the disclosed technology, the delay to the onset of data collection can be on the microsecond time scale.

The signature (or trigger event) can be detected using one or more sensors or detectors configured to measure characteristics of the object under observation. The signature (or trigger event) can be one or more of a variety of different measurements taken from one or more sensors or detectors adapted for the event. For instance, the signature (or trigger event) can be indicative of a change of state in the object itself. Furthermore, the sensors or detectors used can be sensors in contact with the object itself (e.g., embedded in the object or in contact with a surface of the object) or can be noncontact sensors.

In certain embodiments, the signature (or trigger event) can be a temperature (or, in some embodiments, a rate of temperature change or an acceleration/deceleration in temperature change) detected by a temperature sensor (e.g., a thermocouple or other temperature sensor associated with the object (e.g., inserted into the object, attached to an exterior surface of the object, and/or attached to the vessel containing the object)). In some embodiments, the signature (or trigger event) can be light produced by the object and detected by a light sensor (e.g., an optical fiber or bundle of fiber optics embedded in and/or oriented around the object and configured to detect a light level (e.g. a photon flux or amplitude, a rate of change thereof, or an acceleration/deceleration in a change thereof)). In further embodiments, the signature (or trigger event) can be strain in the object (or, in some embodiments, a rate of strain change or an acceleration/deceleration thereof) detected by a strain detector (e.g., an optical strain detector or resistance-based strain gauge located in and/or attached to the object). In some embodiments, the signature (or trigger event) can be a sound or sound level emitted by the object under observation (or, in some embodiments a rate of change to sound or an acceleration/deceleration thereof) and detected by a sound sensor (e.g., one or more sound sensors (such as a piezoelectric sensor) embedded in and/or oriented around the object under observation). In further embodiments, the signature (or trigger event) can be a pressure in the vessel containing the object (or, in some embodiments, a rate of change in pressure in the vessel or an acceleration/deceleration thereof) detected by a pressure sensor configured to detect the pressure in the interior vessel. In some embodiments, a signal used to drive the event itself will provide the x-ray and/or image collection trigger. Thus, any of the disclosed embodiments can be used to image stimulated events as well as spontaneous events.

Any of these disclosed sensors can generate a signal (e.g., a voltage) indicative of the property they are sensing (e.g., temperature, light, strain, sound pressure, etc.), and thus the signature or trigger event can be a particular value (or derivative) of the signal (e.g., a particular voltage) produced by the respective sensor.

Any of these disclosed signatures (trigger events) and associated sensors can be used alone or in combination with one another. When multiple measurements are used as part of determining the trigger, appropriate logic can be applied to the measurements and can vary from implementation to implementation and experiment to experiments. In some cases, for instance, x-ray activation may occur when any one of multiple measurements reaches a corresponding threshold value (e.g., the trigger is based on OR logic for multiple input measurements); or multiple threshold values must be reached before triggering x-ray activation (e.g., the trigger is based on AND logic for multiple input measurements); or combinations of OR and AND logic are used (e.g., "IF A or (B and C), THEN trigger x-ray activation). Further, the particular threshold values used for the trigger events will depend on the experiment and object under consideration. In embodiments of the disclosed technology, the thresholds are user adjustable and can be set as appropriate for the particular event to be imaged. In general, a triggered, gridded x-ray system such as described above can be used to image a wide variety of dynamic, spontaneous or stimulated events.

In one particular implementation, which was adapted for observing HE events, the system comprises a 100 kVp, 800 mA gridded (grid controlled) x-ray source which can remain armed for minutes without heating the anode and then be triggered within several microseconds to allow x-ray generation with flux sufficient to penetrate an object which has a total path integrated areal density of ~7 g/cm². Areal density is the spatial line integral of density.

Figure 3:
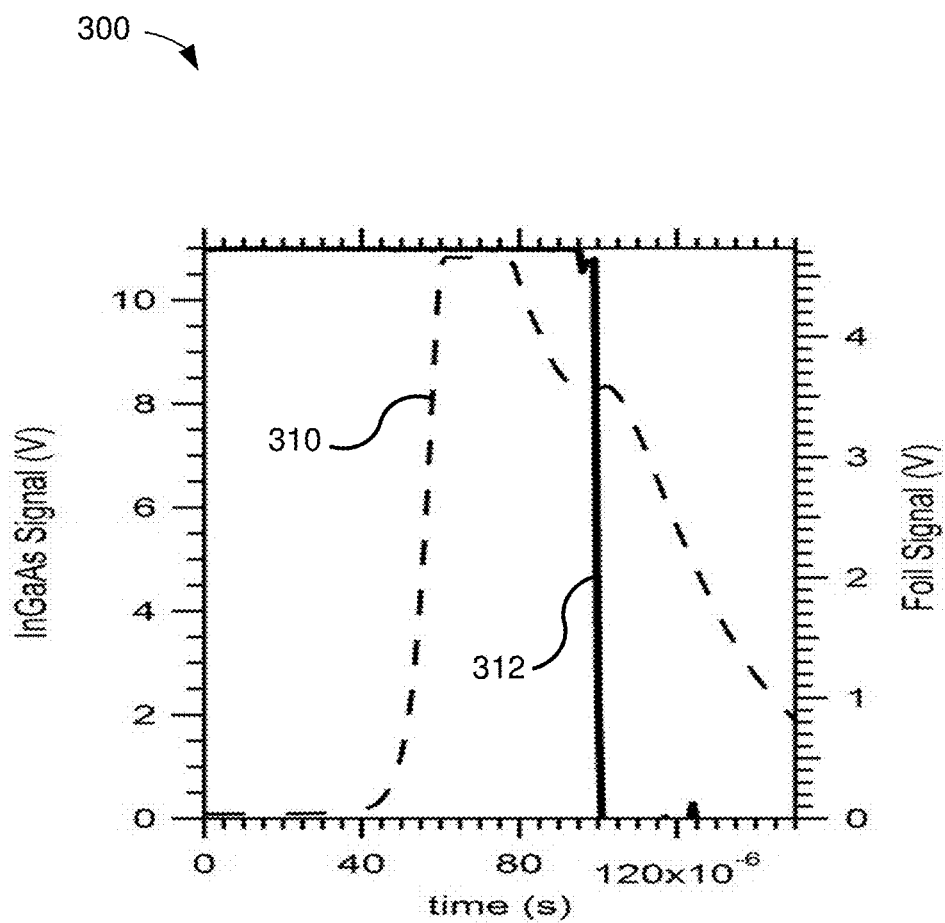
FIG. 3 is a graph showing the rise in Planck greybody emission at the center of a high explosive observed through the IR-band light emitted in the central region of HE as measured via a multimode fiber-optic coupled to an amplified InGaAs photodiode for an example embodiment.

FIG. 3 is a graph 300 that includes plot 310 that shows the rise in Planck greybody emission at the center of the HE observed through the IR-band light emitted in the central region of HE as measured via a multimode fiber optic coupled to an amplified InGaAs photodiode according to one example embodiment. Also shown in FIG. 3 is plot 312 corresponding to the breakfoil signal which indicates the time at which the case encasing the HE ruptures and is generally considered to be the end of the experiment, although images collected after this time may still be useful in understanding case failure. More specifically, for the experimental setup illustrated by FIG. 3, the InGaAs photodiode was coupled to an oscilloscope. FIG. 3 thus shows oscilloscope voltages recorded before and during ignition. The dashed black line is the InGaAs photodiode output and the solid black line is a breakfoil voltage demonstrating time at which the case has come apart. These observables were measured directly on an oscilloscope with microsecond time resolution for a duration of seconds and captured the switch in timescales between the pre-ignition and post-ignition regimes.

In this particular example, the oscilloscope's internal triggering circuitry was used to generate a TTL pulse from either the thermocouple or InGaAs channels with appropriate levels and filtering chosen to balance pre-trigger stability with trigger sensitivity. For instance, for this particular example, a voltage level at or about 100 mV or above was used for when the thermocouple was used as a trigger, and a voltage level at or about 25 mV or above was used for when a fiber optic coupled to an InGaAs photodiode was used as the trigger These particular values are by way of example only and will vary depending on the material under consideration and the experimental setup. The oscilloscope TTL pulse was used to trigger activation of the x-ray source and the recording of images by the camera.

Although the example embodiment described above used logic circuitry in an oscilloscope to detect when a trigger condition was reached and for generating the trigger signal to the x-ray source and the camera, other configurations are possible. For instance, a variety of logic circuits can be used to provide such threshold detection and signal generation (e.g., an application specific integrated circuit (ASIC), field programmable gate array (FPGA), components of a printed circuit board (PCB), or any other electronic components configured to provide such detection/trigger signal functionality). Such logic circuits can be configured to be user adjustable in order to allow a user to tailor the trigger events for a particular object under observation, a particular combination of one or more sensors and measurements, and/or a particular experiment.

D. Source

This section describes example x-ray sources that can be used in embodiments of the disclosed technology (e.g., any embodiment disclosed herein, such as the example configurations shown in FIGS. 4, 5, and 6). The particular sources disclosed, however, should not be construed as limiting, however, as other sources can also be used with the disclosed technology.

The x-ray source can vary from implementation to implementation. In one example implementation, the x-ray system is a pulsed fluoroscopy system with a gridded tube which is held in its "armed" state with the filament on, the anode rotating, high accelerating voltage, and high grid voltage. It can be held in this state for minutes or longer without generating x-rays as the grid voltage prevents the electrons from the filament from reaching the anode. For instance, the internal explosive temperature can be monitored and, when it is in thermal runaway, the x-ray system put into the armed state. The final switch in time scale exhibited by the material as ignition begins then triggers the x-ray grid to turn off, thus triggering the generation of x-rays (e.g., with 100 or higher kVp and 500 mA or higher anode current (such as 800 mA)). Any of the triggering techniques described above can be used to detect and provide the x-ray activation signal to turn the x-ray grid off. This provides, for example, a high flux x-ray source for a duration of milliseconds. The exact pulse width is determined by the duration of the TTL pulse sent to the x-ray grid circuit.

In some cases, the "armed" state of the x-ray system is achieved through depression of a "dead man" button or other arming switch that may be activated when the object nears the event to be monitored. In certain embodiments, any of the disclosed triggering techniques discussed above can also be used to monitor and detect a trigger condition for arming the x-ray system in addition to monitoring and detecting a trigger condition for activating the x-ray system from its "armed" state.

In some embodiments, a continuously operating x-ray source such as a microfocus source can be used to provide long duration, continuous x-ray illumination of the object. In further embodiments, pulsed x-ray sources with intermediate duration such as portable veterinary sources with duration of seconds can be used or pulsed x-ray sources with tens of nanosecond duration and tens of hertz repetition rates.

E. Detection

This section describes example detection mechanisms and/or techniques that can be used in embodiments of the disclosed technology (e.g., any embodiment disclosed herein, such as the example configurations shown in FIGS. 4, 5, and 6). The particular mechanisms disclosed, however, should not be construed as limiting, however, as other detectors and/or imaging techniques can also be used with the disclosed technology.

In certain example embodiments, the high energy x-rays are converted to light using a CsI scintillator (or other scintillator) with ~microsecond primary decay time and an ultrafast video camera to capture the dynamic x-ray transmission movie. The imaging system uses a high-speed video camera that is capable of microsecond interframe times and can be triggered to capture both pre- and post-trigger frames (e.g., by using frames already buffered into a cyclic memory buffer). In certain embodiments, the same trigger mechanism that activates x-ray generation (e.g., turns off the x-ray grid) also provides a trigger to the high-speed video camera. Current x-ray flux, source-to-detector distances, and scintillator and optical efficiencies enable images to be collected with sufficient signal-to-noise to resolve density changes on the order of a few percent with time resolution on the order of 5 microseconds. The spatial resolution is generally controlled by the x-ray focal spot size and the source-object-detector distance. For instance, one example configuration using a 1 mm large focal spot and a source-to-detector distance of 200 mm yields a spatial resolution on the order of hundreds of microns. The source-to-detector distance can be determined at least in part by the experiment being run. For instance, in the case of imaging thermal explosions in secondary high explosives (HE), the distance is determined in part by the desire to contain explosively generated fragments from damaging either source or detector. Non-explosive experiments would allow smaller source to detector distances and, consequently, higher fluxes for faster imaging or higher spatial resolutions. For slower events, continuous microfocus sources can be used providing higher spatial resolution of micron scale.

F. Example Configurations and Methods of Use

FIG. 4 is a schematic block diagram 400 of an example spontaneous dynamic x-ray radiography system in accordance with the disclosed technology. In the illustrated embodiment, the example system (e.g., the example LARS system) comprises a camera 410, a lens 412, a scintillator 414, a vessel 416 used for thermal-explosion studies, an object 418 of study in the vessel, and an x-ray generator 420. These components can vary from embodiment to embodiment and can be any of the example components or configurations disclosed above or elsewhere herein.

FIG. 4 also shows several variables available for adjustment and optimization depending on the system and experiment. The illustrated variables include, for instance, one or more of kVp (accelerating voltage), mA (the electron beam current), Ss (the anode spot size illuminated by electrons), a and b (distances from source, object and scintillator), $\lambda$ the optical conversion wavelength of the detector), OD (the optical density of the object), QE (the quantum efficiency of the camera sensor at $\lambda$, r (the image radius defining the aperture solid angle), F (the f stop of the complex lens system), and/or $\tau$ (the integration time).

The illustrated system further includes trigger logic (trigger controller) 440, which is configured to provide a trigger mechanism for activating x-ray generation and/or image/video capture as disclosed herein. As discussed above, the trigger logic can be configured to receive one or more trigger signals from one or more sensors (e.g., sensor 442) coupled to or near the object itself and to generate an activation signal for the x-ray generator 420 and/or an activation signal for the camera 410 in response therefore. Any of the example triggering mechanisms and/or sensors discussed above or elsewhere herein can be used in embodiments of the disclosed system 400.

In the illustrated embodiment, the x-ray generator 420 is a gridded (or grid controlled) x-ray source. The x-ray generator can be configured to transition from an armed state into an x-ray generation state upon receipt of the trigger signal, the armed state being a state in which a cathode 422 and an anode 424 of the x-ray source are active but electrons are deflected from interaction with the anode 424 through a voltage applied to grid 426 of the gridded x-ray tube. For instance, the trigger signal can cause a grid voltage in the gridded x-ray tube to change into a state that permits electrons from the cathode 422 in the x-ray source to strike the anode 424 in the x-ray source, thereby generating x-rays.

The illustrated system 400 further includes a processing system 430 in communication with the camera 410 (which operates as a video capture system for the illustrated embodiment). The processing system 430 can be, for example, a computer system comprising one or more processors (processing units) configured to execute computer-executable instructions stored on one or more tangible, non-transitory computer-readable media (e.g., one or more optical media discs, volatile memory components (such as DRAM or SRAM), or nonvolatile memory or storage components (such as hard drives and solid state drives (e.g., Flash drives)). The computer system can be configured or programmed (e.g., using instructions stored on the computer-readable media) to implement an imaging process that is performed after the camera captures video data from the spontaneous or stimulated event and that receives, renders, and outputs (e.g., via display on a display device or storage in a suitable image file) the images captured by the camera during the spontaneous event. Such imaging software is known and need not be described in detail here.

FIG. 5 is another schematic block diagram 500 showing a detailed cross-sectional view an example table top system (e.g., a system as in FIG. 4). For example, the block diagram shows a camera 510, a lens 512, a scintillator 514, a vessel 516 used for thermal-explosion studies (with windows 515, 517 in apertures of the vessel 516 that allow for imaging of the object of study), an object 518 of study in the vessel, and an x-ray generator 520. The windows can be made of any low atomic number material transparent to x-rays, such as carbon fiber, aluminum, or a combination of carbon fiber plates and aluminum plates (e.g., a ¼ inch carbon fiber window, potentially with a ⅛ inch aluminum plate). Windows transparent to visible light, such as lexan, can also be used.

FIG. 6 is an image 600 of an actual LARS embodiment on a table top. In the illustrated embodiment, LARS comprises a camera 610, a scintillator 612, a vessel 614 used for thermal-explosion studies (with windows 613, 615 in apertures of the vessel 614 that allow for imaging of the object of study (not shown)), and an x-ray tube 616. In this example implementation, the camera 610 is a high-speed Phantom camera from Vision Research Inc., the scintillator 612 is a CsI scintillator from Radiation Monitoring Devices, Inc., (RMD), and the x-ray tube 616 is an x-ray source with a gridded x-ray tube from CoRE labs, LLC. These particular components should not be construed as limiting, as the system can be implemented using various other suitable components from other providers, including a direct conversion x-ray camera with no scintillator.

As noted above, FIG. 6 also shows an image intensifier 620 and a turning mirror 622. The image intensifier 620 can optionally be used with the camera 610 as part of the video capture system (primarily comprising the camera). The turning mirror 622 can optionally be used to redirect light from the scintillator so that one or more components of the video capture system (e.g., the camera 610 and image intensifier 620) can be placed out of the x-ray beam path of the x-ray source. For instance, the turning mirror 622 can reflect the output of the scintillator at an angle away from the x-ray beam path, and the camera 610 and any associated components can be placed along the reflected path so that its electrical components are not directly exposed to the x-ray beam.

Figure 8A:
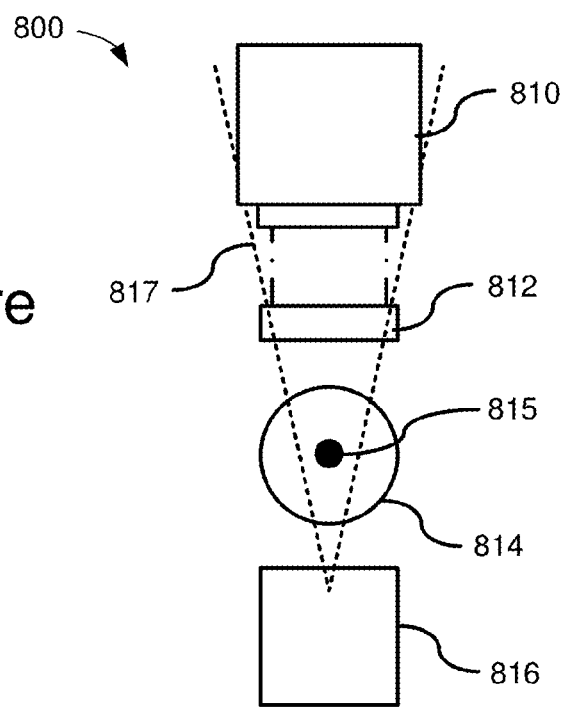
FIGS. 8A and 8B are schematic top-down views of an example x-ray radiography system having a turning mirror in accordance with the disclosed technology.
Figure 8B:
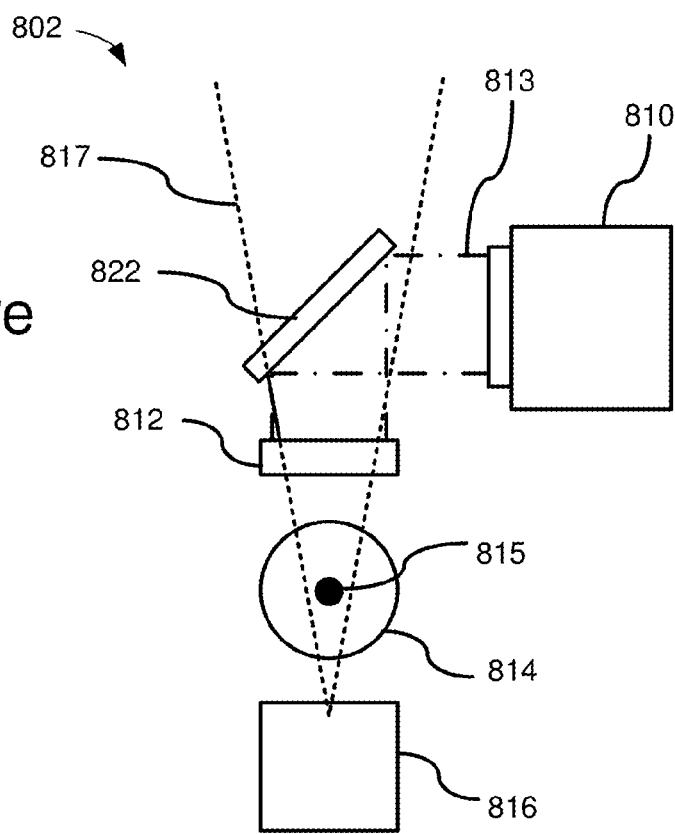

FIGS. 8A and 8B, for example, are schematic top-down views 800, 802 of an example x-ray radiography system that illustrates the benefit of the turning mirror (e.g., turning mirror 622). In FIGS. 8A and 8B, the example x-ray radiography system comprises a camera 810, a scintillator 812, a vessel 814 containing the object 815 being imaged, and an x-ray source 816. FIG. 8A also shows an x-ray beam path 817 emanating from the x-ray source 816. As can be seen, in FIG. 8A, the x-ray beam path 817 passes through camera 810, potentially affecting or damaging its internal components and/or operation. FIG. 8B shows insertion of a turning mirror 822 into the system. In the illustrated embodiment, the turning mirror 822 is rotated approximately 45 degrees and the camera 810 is located at a right angle such that its lens receives the image produced at the scintillator 812 (shown as image path 813). In this configuration, the x-ray beam path 817 no longer passes through or interferes with the camera 810.

The table top nature of certain embodiments of the disclosed technology allow for optimizing the exact set up for spatial resolution/field of view, penetration depth, contrast sensitivity, and/or time resolution desired for a specific application. Tradeoffs between these parameters can be made. For instance, binning pixels reduces spatial resolution but increases signal to noise and therefore the contrast sensitivity; spatial resolution can be recovered at the cost of field of view by placing the object closer to the x-ray source and further from the detector to increase x-ray magnification; and/or optical magnification after the scintillator can be used to match the image size on the scintillator to the camera chip size. Also available for optimization are x-ray energy with higher energy increasing x-ray flux and enabling penetration through larger/denser samples, but decreasing x-ray contrast in the low density object.

Embodiments of the table top system disclosed herein allow extreme flexibility in experiment design. Increasing integration time improves signal to noise, enabling greater contrast sensitivity at the cost of temporal resolution. The converse is also true. The exact tradeoff between all these parameters can be easily tuned to optimize data collection for each particular instance and application. Furthermore, multiple cameras can be used when viewing the scintillator at off-normal axes to allow for simultaneous imaging with different parameters (e.g., a high resolution/low field of view camera and a low resolution/high field of view camera).

As will be appreciated, a variety of x-ray radiography systems and configurations are possible in accordance with the disclosed technology. One example embodiment of the disclosed technology is a system comprising: an x-ray source, the x-ray source comprising a gridded x-ray tube; a scintillator positioned to receive x-rays generated by the x-ray source; a video capture system configured and arranged to, when activated, capture and store image data produced by the scintillator for multiple consecutive frames; and an object to be x-ray imaged using the x-ray source, the scintillator, and the video capture system, the object being located between the x-ray source and the scintillator. The system can be sized and configured to fit on a table top (e.g., the system can have a size of 10 ft.×10 ft. or smaller, 6 ft.×6 ft. or smaller, or 3 ft.×3 ft. or smaller). The system can further comprise a containment vessel located between the x-ray source and the scintillator, the containment vessel being configured to hold the object to be x-ray imaged. In some embodiments, the system further comprises a trigger mechanism for providing a trigger signal that causes the x-ray source to begin generating x-rays. In such embodiments, the x-ray source can be configured to transition from an armed state into an x-ray generation state upon receipt of the trigger signal, the armed state being a state in which a cathode and an anode of the x-ray source are active but electrons are deflected from interaction with the anode through a voltage applied to the gridded x-ray tube. For instance, the trigger signal can cause a grid voltage in the gridded x-ray tube to change into a state that permits electrons from a cathode in the x-ray source to strike an anode in the x-ray source, thereby generating x-rays. In some implementations, the trigger mechanism comprises: one or more sensors configured to sense a characteristic of the object to be imaged; and one or more hardware logic components (e.g., dedicated hardware logic components or logic components of an oscilloscope) in communication with the one or more sensors and configured to generate the trigger signal when the one or more sensors produce one or more signals indicating that a trigger threshold has been reached. In some implementations, the one or more sensors include one or more of a sensor located within the object; a sensor positioned in contact with a surface of the object; and/or a sensor positioned proximate to but not in contact with the object. Further, the one or more sensors include one or more of a temperature sensor, light sensor, strain sensor, pressure sensor, or sound sensor. In some implementations, the x-ray source is adapted from a fluoroscopy x-ray source.

Another example embodiment is a system comprising: an x-ray source; a scintillator positioned to receive x-rays generated by the x-ray source; a video capture system configured and arranged to, when activated, capture and store image data produced by the scintillator for multiple consecutive image frames; an object to be x-ray imaged using the x-ray source, the scintillator, and the video capture system, the object being located between the x-ray source and the scintillator; and a trigger mechanism for providing a trigger signal that causes the x-ray source to begin generating x-rays, the trigger mechanism comprising one or more sensors configured to sense a characteristic of the object to be imaged, and one or more hardware logic components in communication with the one or more sensors and configured to automatically generate the trigger signal when the one or more sensors produce one or more signals indicating that a trigger threshold has been reached. The system can be sized and configured to fit on a table top (e.g., the system can have a size of 10 ft.×10 ft. or smaller, 6 ft.×6 ft. or smaller, or 3 ft.×3 ft. or smaller). The system can further comprise a containment vessel located between the x-ray source and the scintillator, the containment vessel being configured to hold the object to be x-ray imaged. In some implementations, the one or more sensors include one or more of: (d) a sensor located within the object; (e) a sensor positioned in contact with a surface of the object; or (f) a sensor positioned proximate to but not in contact with the object. The one or more sensors include one or more of a temperature sensor, light sensor, strain sensor, pressure sensor, or sound sensor.

Another example embodiment is a system, comprising: an x-ray source; a video capture system having a direct detection x-ray camera, the video capture system being configured and arranged to, when activated, capture and store image data produced by x-ray detected by the direct detection x-ray camera for multiple consecutive image frames; an object to be x-ray imaged using the x-ray source and the video capture system, the object being located between the x-ray source and the video capture system; and a trigger mechanism for providing a trigger signal that causes the x-ray source to begin generating x-rays, the trigger mechanism comprising one or more sensors configured to sense a characteristic of the object to be imaged, and one or more hardware logic components in communication with the one or more sensors and configured to automatically generate the trigger signal when the one or more sensors produce one or more signals indicating that a trigger threshold has been reached. The system can further comprise a containment vessel located between the x-ray source and the scintillator, the containment vessel being configured to hold the object to be x-ray imaged. In some implementations, the one or more sensors include one or more of: a sensor located within the object; a sensor positioned in contact with a surface of the object; or a sensor positioned proximate to but not in contact with the object. The one or more sensors include one or more of a temperature sensor, light sensor, strain sensor, pressure sensor, or sound sensor.

Figure 21:
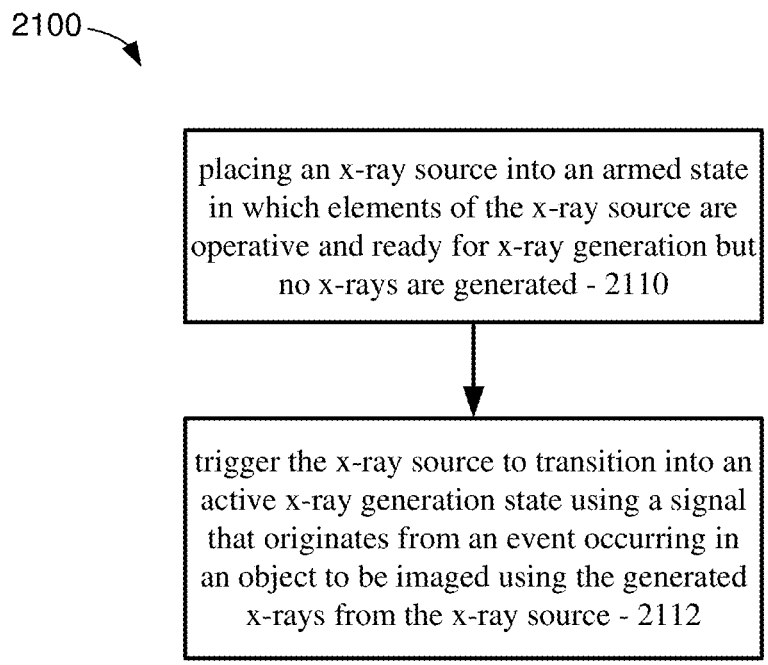
FIGS. 21-22 are diagrams showing example methods for using embodiments of the disclosed technology.

FIG. 21 is a flow diagram 2100 illustrating one example method for operating a radiography system as disclosed herein. At 2110, an x-ray source (e.g., a gridded or grid controlled x-ray source) is placed into an armed state in which elements of the x-ray source are operative and ready for x-ray generation but no x-rays are generated. At 2112, the x-ray source is triggered to transition into an active x-ray generation state using a signal that originates from an event occurring in an object to be imaged using the generated x-rays from the x-ray source. The signal can be produced using hardware logic components that are coupled to one or more sensors configured to detect occurrence of the event in the object. At least one of the one or more sensors can be in contact with the object. In some implementations, the object to be imaged is an explosive material and the event is an onset of an explosion of the explosive material during a period of thermal runaway experienced by the explosive material. In other implementations, the object to be imaged is a material being strained and the event is an onset of a material failure of the material being strained. In further implementations, the object to be imaged is a material experiencing an exothermic reaction and the event is an onset of the exothermic reaction. In some implementations, activation of a video capture system configured to produce x-ray transmission images of the object is triggered in response to the generated x-rays from the x-ray source. For example, the video capture system can also be activated by the signal that is generated from the event occurring in the object to be imaged.

Figure 22:
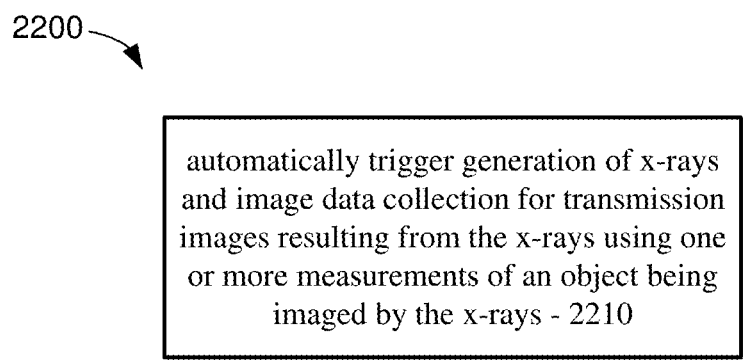

FIG. 22 is a diagram 2200 illustrating another example method for operating a radiography system as disclosed herein. At 2210, generation of x-rays and image data collection for transmission images resulting from the x-rays is automatically triggered using one or more measurements of an object being imaged by the x-rays. The measurements can, for example, indicate a change of state in the object. In some implementations, the object is an explosive material and the measurements indicate that the object has entered a state of explosion. In other implementations, the object is a material being strained and the measurements indicate that the object has entered a state of material failure. In further implementations, the object is a material experiencing an exothermic reaction and the measurements indicate that the object has entered a state of exothermic reaction. The measurements can be obtained from one or more sensors embedded into the object, sensors in contact with a surface of the object, and/or sensors not in contact with the object but configured to directly sense or detect a characteristic of the object. In some implementations, the generation of x-rays is performed by a gridded x-ray source, and image data collection is performed by a video camera. In such cases, the x-ray source and the video camera operate as part of an x-ray transmission imaging system in which x-rays interrogate the object and are detected by a scintillator, the scintillator producing light signals captured and recorded by the camera in the form of continuous video data comprising multiple consecutive frames.

G. Example Results

This section describes results from an experiment performed using an example embodiment of the disclosed technology. The particular experiment performed involved imaging thermal explosions in secondary high explosives (HE), but this application should not be construed as limiting as the disclosed system and techniques can be used for a variety of applications in which imaging of dynamic, spontaneous events is desired.

Figure 7:
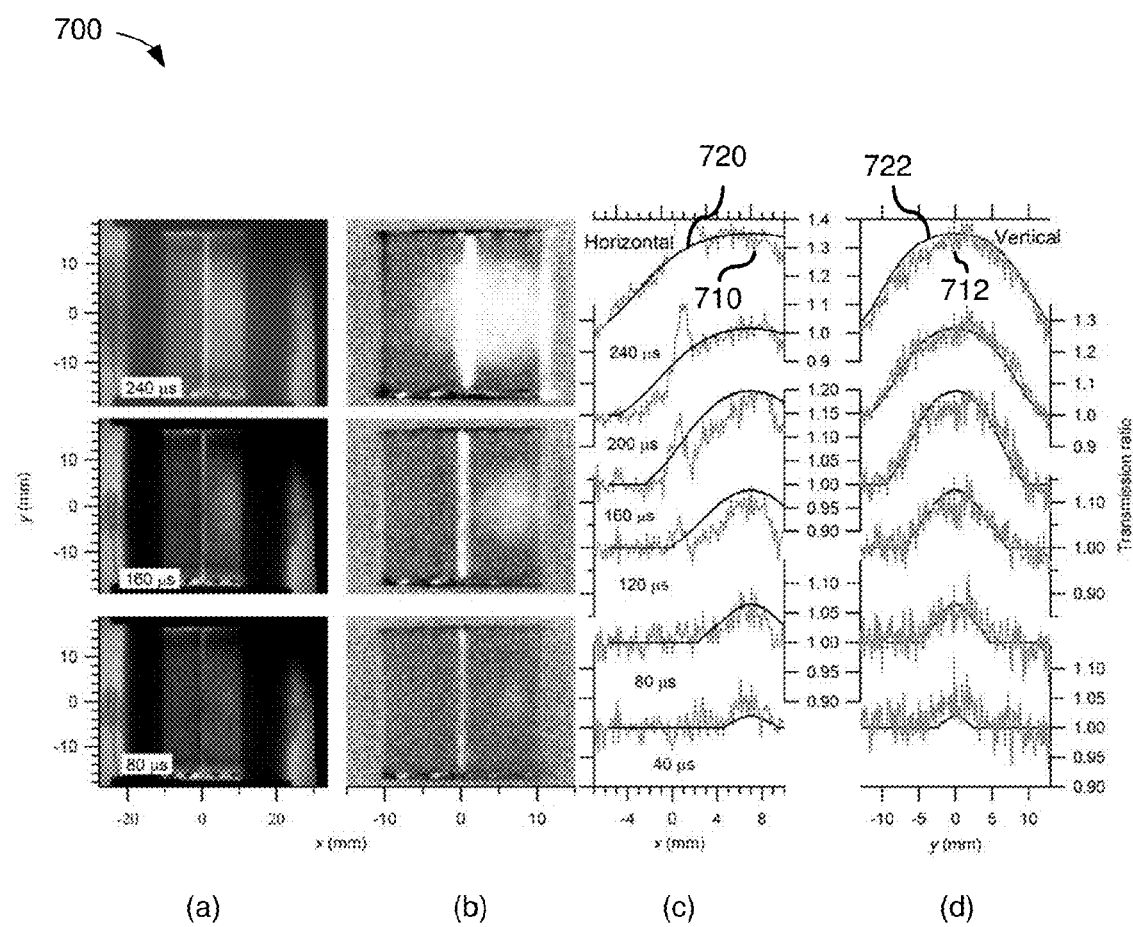
FIG. 7 shows transmission images taken transverse to the cylinder axis of the cased explosive and obtained using an embodiment of the disclosed table-top spontaneous dynamic x-ray radiography system in accordance with the disclosed technology.

FIG. 7 is a series 700 of images and graphs showing results from the experiment. In particular, FIG. 7 shows the transmission images taken transverse to the cylinder axis of the cased explosive. Several frames are shown from the continuous video collected. In column (a) images are shown in direct x-ray transmission. Column (b) of FIG. 7 shows the same frames divided by a static frame collected prior to the dynamic event. These frames are proportional to the change in transmission and more clearly show the increase in transmission in the explosive as the thermal explosion propagates. This is caused by the consumption of solid explosive and release of gas products. Columns (c) and (d) show line profiles from the change in transmission data, which enable quantitative comparisons of data and models.

More specifically, FIG. 7 shows X-ray transmission, change in transmission, and line profiles taken during a thermal explosion in an HMX based plastic bonded explosive formulation. Column (a) shows direct transmission viewed side on with frame times relative to the trigger labeled in the figure, column (b) shows the same images as (a) shown as a ratio to static images taken before ignition, column (c) shows line profiles (grey) (one example of which is shown at 710) obtained by integrating a 2 mm wide path vertically through the region of high transmission at about x=5 to 8 mm in the 80 μs image, and column (d) shows line profiles (grey) (one example of which is shown as 712) obtained integrating a 2 mm wide path horizontally through the image about y=0. Black lines (examples of which are shown at 720, 722) are guides to the eye.

Observation of the evolution of density during the explosion enables inference of the mechanism of material consumption and energy release rate. The mechanism can be input into models which can then be used to simulate the radiographic density results to validate the models. The energy release rate of an explosive is also very helpful to understanding and predicting the thermal response of the explosive. This is one of the questions which drove the development of the disclosed radiographic techniques. There are many other areas where a spontaneous dynamic radiographic capability have is applicable. Other problems we have looked at include solid rocket burning, material failure, and problems in explosives involving the transition to detonation.

H. Further Embodiments

Spontaneous events are those which happen on their own time clock, as opposed to a stimulated or triggered event which is induced to occur by the application of an impulse, such as voltage, impact, etc. Dynamic radiography using embodiments of the disclosed technology can be performed for a stimulated event as well as a spontaneous event. For a spontaneous event, the timing of the event is unknown and the onset of the event is desirably used to trigger the start of the x-ray source. Capturing dynamic radiography of a stimulated event can be done by using the same signal which drives the stimulation (such as a TTL pulse) to both start the x-ray source (and image/video collection) as well as to start the event. In particular embodiments, a delay generator can even be used to start the x-ray source and/or image/video capture system several microseconds or more before starting the event. Any of the embodiments disclosed herein can be applied to stimulated or triggered events in addition to spontaneous events.

In general, the embodiments of the disclosed technology can be adapted for different applications by altering the imaging duration and the spatial resolution of the images. For example, embodiments of the disclosed system can be adjusted or modified to effect different compromises between time resolution and duration and spatial resolution. For instance, the pulsed x-ray system described in the previous sections can provide microsecond time resolution with a few hundred micron spatial resolution for a duration of 100 milliseconds. The resolution and timing can be improved as new x-ray scintillators which are faster and brighter and higher flux x-ray sources and better light collection systems become commercially available. For events with durations shorter than 2 microseconds, flash x-ray units with 25-50 nanosecond duration pulses can be used which can operate at 10 Hz or more and provide a similar several hundred micron spatial resolution. For events with longer durations, portable x-ray heads with 4-6 second duration or longer can be used to provide tens of microsecond time resolution. For even longer duration events, continuous x-ray sources such as microfocus sources can be used to provide millisecond resolution with unlimited duration (hours or longer).

A table below describes several example configurations and capabilities for embodiments of the disclosed.

TABLE 1

| Time resolution (per video frame) | Duration of video capture | Spatial resolution | System description |
|---|---|---|---|
| 50 ns | 50 ns/10 Hz | 300 microns | Flash x-ray heads |
| 2 µs | 100 ms | 200 microns | Pulsed x-ray system |
| 50 µs | 4 s | 300 microns | Portable x-ray system |
| 1 ms | Unlimited (but computer memory typically limits length) | 80 microns | Continuous x-ray |
| 100 ms | Unlimited (but computer memory typically limits length) | 10 microns | Continuous x-ray |

In still further embodiments, transmission images can be converted to density by applying calibrations. This can be done by including a density calibration target of similar atomic number and encompassing the areal density range of the object in the same frame as the object and then calibrating density as a function of transmission from the image.

1. Multi-Axis Radiography Embodiments

In further embodiments of the disclosed technology, multiple imaging systems are used to image a common object. For example, certain embodiments use multiple axes which enables either multiple angle views of an event, or the use of different configurations on different axes to allow, for example, high time resolution along one axis and long duration along another axis. In this way, the highest time resolution and longest duration can be simultaneously acquired to bridge the various time scales associated with an event (e.g., to bridge the time scale associated with heating and the time scale associated with ignition/explosion). Multiple views of a single event with either the same or different spatial and temporal resolution can be acquired.

Figure 9:
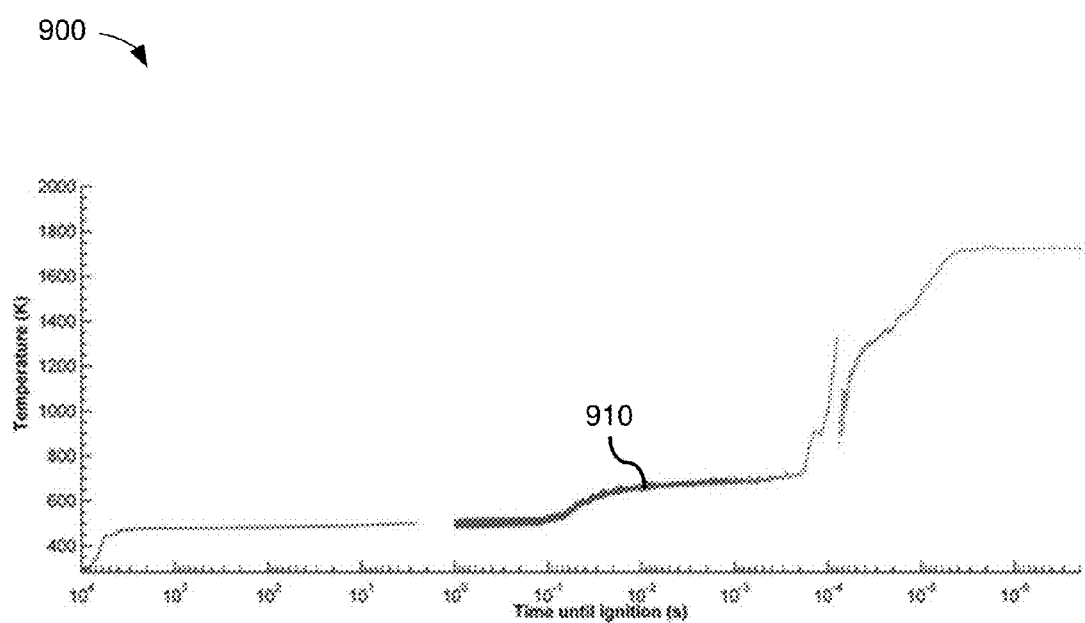
FIG. 9 is a graph showing a plot of object temperature over time for an example application where different time resolution/duration axes were used to image the object.

FIG. 9 is a graph 900 showing a plot 910 of object temperature over time for an example application where different time resolution/duration axes were used to image the object. The plot 910 shows temperatures during the heating of an energetic material from room temperature to explosion with a duration of hours and a final change in material state occurring over microseconds (spanning a dynamic range of over 10 orders of magnitude in time). In graph 900, time scale switches are also shown that show the heating of energetic material over hours ($10^4$ seconds) with thermal runaway occurring in fractions of a second and thermal explosion occurring over microseconds. As can be seen, the dynamic range of this process spans over tens orders of magnitude in time.

Figure 10:
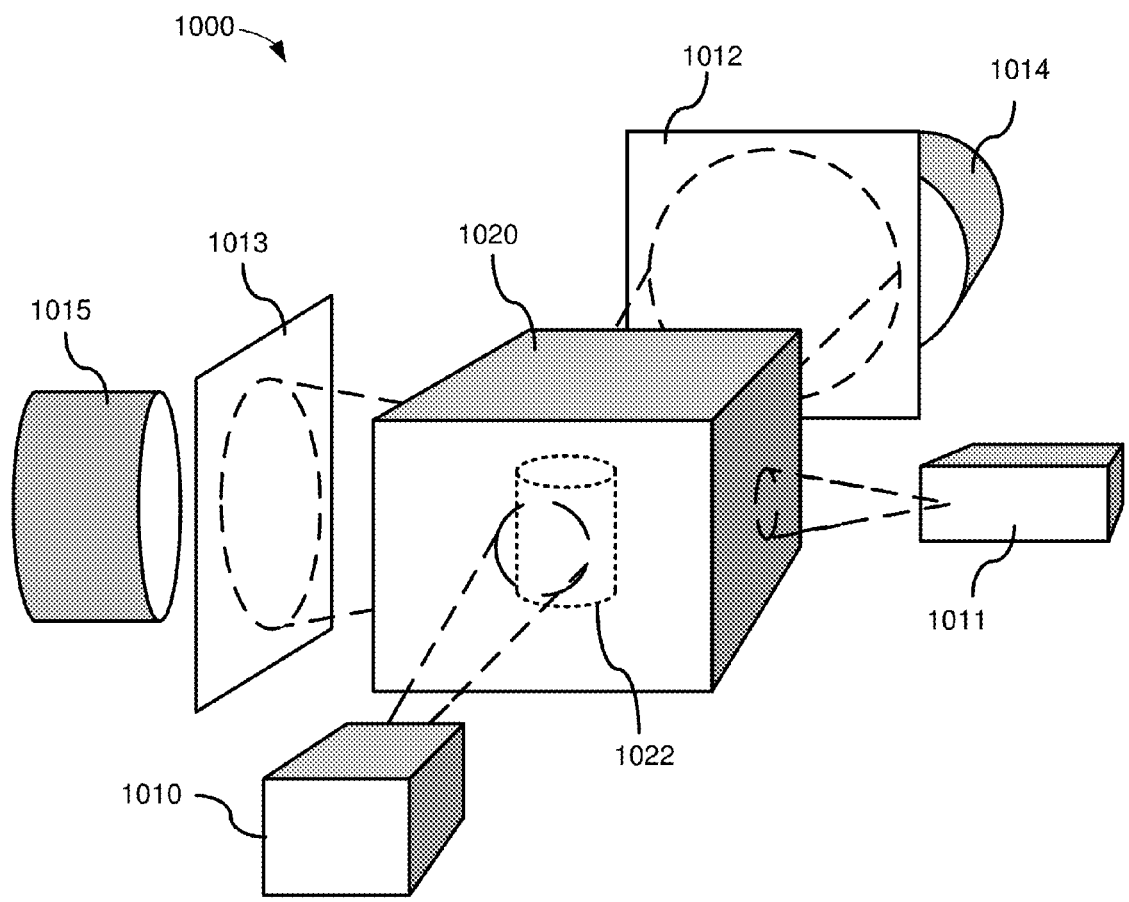
FIG. 10 is a schematic block diagram of an example multi-axis configuration in accordance with an embodiment of the disclosed technology.

FIG. 10 is a schematic block diagram of an example multi-axis configuration 1000 in accordance with an embodiment of the disclosed technology. More specifically, FIG. 10 includes a first x-ray source 1010, first scintillator 1012, and first camera 1014, as described herein. The first x-ray source 1010, scintillator 1012, and camera 1014 can be arranged to interrogate and image an object 1022 contained within vessel 1020 as discussed herein. FIG. 10 also includes a second x-ray source 1011, second scintillator 1013, and second camera 1015 that are also arranged to interrogate and image the object 1022 along a separate axis of the vessel 1020. The second x-ray source 1011, scintillator 1013, and camera 1015 effectively operate as a separate imaging system for the same object and can be configured to operate independently and using, for example, a variety of different settings than the components of the first system. For instance, the second x-ray source 1011, scintillator 1013, and camera 1015 can be configured to operate using a continuous x-ray source, with slower time resolution, and/or finer spatial resolution than the first x-ray source 1010, scintillator 1012, and camera 1014, or vice versa. By way of example, the two systems illustrated can each operate using any of the example configurations shown in Table 1. In this way, the multi-axis configuration 1000 can be used to obtain the benefits of both the continuous x-ray source imaging (with its longer-term imaging and finer spatial resolution) as well as the high-energy imaging using pulsed x-rays for spontaneous events (with its shorter overall duration but very fast time resolution and good spatial resolution).

Such a configuration was used, for example, to obtain the results illustrated in FIG. 9. Subsection III.H.2 below describes in more detail the background, system configuration, and results shown in FIG. 9.

An example embodiment of a multi-axis radiography system as disclosed herein comprises: a first x-ray source; a first scintillator positioned to receive x-rays generated by the x-ray source; a first video capture system configured and arranged to, when activated, capture and store image data produced by the first scintillator for multiple consecutive frames; a second x-ray source; a second scintillator positioned to receive x-rays generated by the second x-ray source; a second video capture system configured and arranged to, when activated, capture and store image data produced by the scintillator for multiple consecutive frames; and an object to be imaged being located between the first x-ray source and the first scintillator, and also being located between the second x-ray and the second scintillator, the first x-ray source, the first scintillator, and the first video capture system being arranged to image the object along a first axis, the second x-ray source, the second scintillator, and the second video capture system being arranged to image the object along a second axis. In some implementations, the first x-ray source is a pulsed x-ray with at least 60 kVp, and the second x-ray source is a continuous x-ray source. In some implementations, the first video capture system is configured to image the object with faster time resolution than the second video capture system. In further implementations, the first video capture system is configured to image the object over a shorter duration than the second video capture system. In some implementations, the system further comprises a trigger mechanism for providing a trigger signal that causes the first x-ray source to begin generating x-rays, the trigger mechanism comprising one or more sensors configured to sense a characteristic of the object to be imaged, and one or more hardware logic components in communication with the one or more sensors and configured to automatically generate the trigger signal when the one or more sensors produce one or more signals indicating that a trigger threshold has been reached. The trigger mechanism can be configured to trigger the first x-ray source but not the second x-ray source.

2. Example Systems, Techniques, and Results from Following Reaction Progress from Thermal Decomposition to Ignition and Internal Burning This section discusses the experimental observation of thermodynamic state variables during the thermal decomposition and evolution of thermal explosion in energetic materials. The continuous measurement of these observables across time scales bridging the pre-ignition thermal decomposition regime and the post-ignition burn propagation regimes are discussed. Techniques for measuring temperature and density continuously are also discussed and results presented for thermal explosions in the HMX based formulation, PBX-9501. Comparisons between the observables and rates of change are also disclosed. These observations can be used to offer a definition of ignition which distinguishes between the slow processes of thermal decomposition and heating and the switch to fast consumption of solid by internal burning.

The response of energetic materials to temperature occurs over time scales ranging from microseconds to hours. This represents a dynamic range of nearly 10 orders of magnitude in time, making energetic materials extremely challenging to study both experimentally and computationally. Experimentally, following observables such as temperature, density, and pressure with microsecond resolution for durations of hours is not typically possible.

Figure 11:
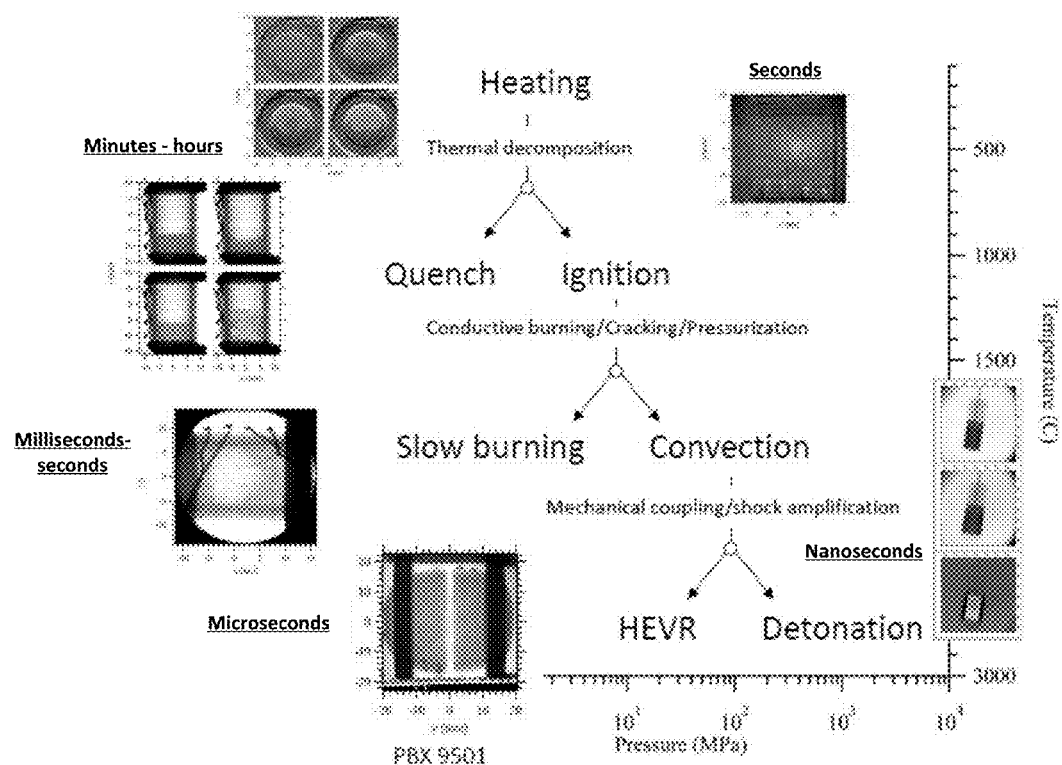
FIG. 11 is a graph showing a schematic description of the evolution of a thermal explosion showing notionally the effect of temperature and pressure.

FIG. 11, for example, is a graph 1100 showing a schematic description of the evolution of a thermal explosion showing notionally the effect of temperature and pressure. Graph 1100 also presents several images of the object obtained using embodiments of the disclosed technology. The particular sets of images shown in FIG. 11 were obtained using different configurations of the disclosed x-ray radiography system and illustrate the range of imaging possibilities available with the system. For instance, each image or image set is labeled in underlined bold-type with the time resolution with which the respective image was obtained. The nanosecond images, for instance, were obtained using the pulsed x-ray configuration discussed above that is adapted for imaging spontaneous (or triggered) explosive events.

Example radiography tools for performing radiography as illustrated in FIG. 11 and results of the observation are discussed in more detail below. In the discussion below, the material that was imaged evolved through the full range of thermal decomposition to ignition, and post-ignition burn propagation. The experimental observables included temperature and density The thermal decomposition of HMX based formulations can be parsed into the slow thermal decomposition, the evolution of ignition, and the post-ignition burn propagation regimes as shown in FIG. 11. This is a very practical way to understand thermal explosions as the time scales for the regimes are dramatically different and require different tools and techniques to study them. Thermal decomposition can occur over hours or longer depending on the temperatures to which the HMX is subjected. If the high explosive (HE) is subjected to a sufficiently high temperature for long enough times, exothermic decomposition can be activated and provide sufficient heating rates to accelerate the decomposition to generate a thermal explosion. The onset of this thermal explosion is often called ignition. Post-ignition burn propagation can occur via either slow conductive propagation through the solid or faster convective propagation through the gas phase.

For HMX based formulations, propagation occurs on the time scale of tens of microseconds. A subsequent even faster regime of detonation is possible if confinement conditions and path lengths sufficient for the deflagration to detonation transition (DDT) are present.

Due to the change in time scales from microseconds to hours covering the multiple regimes, it is difficult to follow a single observable through the entire event. Using embodiments of the technology, however, diagnostics can be monitored for hours with time resolution of microseconds. For example, an approach using multiple radiograph systems (e.g., a multi-axis configuration as shown in FIG. 10) as disclosed herein can be used, each system being calibrated for a different time scale. As more fully discussed below, an embodiment of such a system and the resulting diagnostics has been applied to a number of HMX based formulations in order to continuously monitor the entire evolution of a thermal explosion of the formulation.

Figure 12:
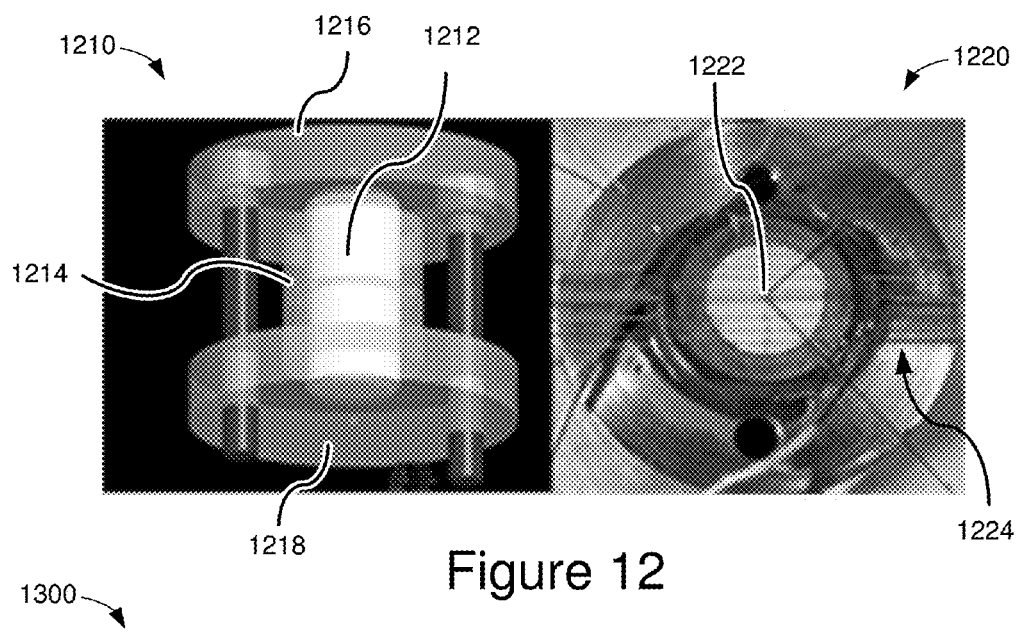
FIG. 12 shows a schematic diagram and photograph of a cylinder with an explosive as used in experiments discussed herein.

The example experimental setup discussed herein used a cylinder of explosive of ½" diameter and 1" height encased in an aluminum cylinder which was held together with either steel bolts or a threaded endcap. The aluminum was then heated using resistive wire heaters. A schematic of the experimental setup is shown in FIG. 12. Pane 1210 illustrates a schematic of the cased experiment with the explosive 1212 located within cylinder 1214 with endcaps 1216, 1218, and pane 1220 shows a photograph of the midplane thermocouple 1222 and fiber optic diagnostics (shown generally at 1224) used in a particular experiment.

Figure 13:
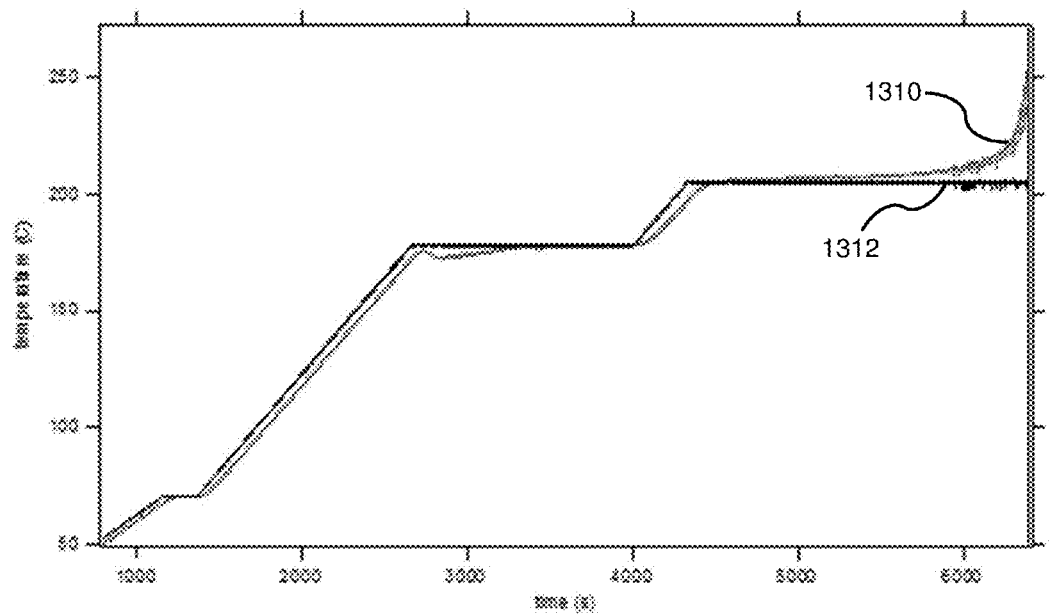
FIG. 13 is a graph showing the standard temperature trajectory used for a thermal explosion experiment discussed herein.

In the example experiment, temperature is measured using thermocouples and broadband near IR pyrometry. The standard temperature trajectory used for a thermal explosion experiment of PBX-9501 is shown in FIG. 13. In particular, plots 1310 (colored) are internal HE temperatures, and plot 1312 (black) shows the aluminum boundary temperature. The sample is heated in several steps with a hold point at ~178° C. to allow sample equilibration after the endothermic beta-delta phase transition of the HMX. A final hold temperature of 205° C. is used. At this temperature, the aluminum boundary is fixed at 205° C. and the PBX-9501 begins to generate heat through exothermic decomposition steps, so that the hottest spot in the material moves from the boundary towards the spot furthest from the metal boundary at the center of the HE cylinder. The regime where the HE temperature exceeds the boundary temperature is called the self-heating regime. The point at which this self-heating rate accelerates several hundred seconds before thermal explosion is the onset of the thermal runaway regime. The final point taken before the sample undergoes a rapid thermal explosion is called the ignition point.

The same data can be plotted on a logarithmic scale to emphasize the dynamic features leading to the thermal explosion. The log time base is plotted as the time until the ignition event, as shown in FIG. 9. The final point on the linear time scale in FIG. 13, defined as the ignition point, is now shown to have significant structure when the time axis is drawn using the log time base in FIG. 9. The data in FIGS. 13 and 9 were taken using fine gauge (75 micron) type K thermocouples measured with microsecond time resolution and with multimode fiber optics coupled to the central region of the HE and measured on an amplified InGaAs photodiode (also with microsecond time resolution).

The structure seen in the logarithmic scale plot is reminiscent of the spatial structure of a flame front above a regressing surface. The jump to ~600-700 K in the tens of millisecond regime is analogous to dark zone burning, and the final jump to 1800 K in the hundreds of microsecond regime is similar to the bright zone. The detailed structure of the ignition regime is sensitively dependent on the distance between the midplane diagnostics and the ignition volume. The ignition volume position was observed to be very sensitive to the boundary conditions of the experiment. Ignition volume size and location were observed using radiography, using embodiments of the disclosed LARS system, as discussed below.

Density during the evolution of thermal explosions was also followed using an embodiment of the disclosed x-ray radiography system. In order to observe the slow evolution of density during the pre-ignition thermal decomposition regime, a radiographic system as described above but with a continuous microfocus x-ray source using a CCD based camera to record images on the 1-10 Hz period was used. The microfocus source can be run continuously for many hours and produces very high spatial resolution images due to the 10-100 micron x-ray spot size available from this type of source. The x-ray radiographs were collected as x-ray transmission images with lower transmission (darker regions) corresponding to higher density or longer path length regions of the sample. The x-ray transmission image is a two dimensional image of the areal density (g/cm$^2$) of the sample which is the path integral of the three dimensional sample density. Because the path length is known, the changes in x-ray transmission can be attributed to changes in material density along the line of sight. Images are presented both as direct transmission, or as change in transmission where an image ratio is made by dividing an image by an image collected earlier in time in order to match the dynamic range of the change in transmission to the dynamic range of the data presentation (color look up table). In both direct transmission and change in transmission, the data is presented with white representing higher transmission and black lower transmission.

FIG. 14 shows the direct transmission image 1410 and change in transmission image 1412 of a PBX-9501 thermal explosion experiment in the axial view (transverse to the symmetry axis). The light spot (shown generally 1420) above the midplane is the volume where solid density is being lost in the seconds leading up to the thermal explosion. This region is sometimes referred to as the ignition volume. For PBX-9501, the ignition volume is typically a clearly defined region with diameter approaching 2 mm and density loss evolving over seconds to a final density change of approximately 8%, which is equivalent to a complete loss of solid density in the 2 mm volume. The red vertical trace 1422 is the line profile across the sample showing the transmission change at the position going through the ignition volume. Changing gas confinement conditions for the experiment changes the appearance, but not the size, of the ignition volume. Additionally, the location of the ignition volume has been found to be sensitive to the boundary conditions and sample environment.

In the illustrated experiment, the density was measured continuously through the pre-ignition thermal decomposition regime, including the measuring case and HE expansion due to the coefficient of thermal expansions of the different materials, and through the volume expansion of the beta-delta phase transition in the HMX. The extra volume at the top and bottom of the case fills in when the material expands at the phase transition, and the gap between the two pellets at the midplane disappears when the material expands and the binder softens at elevated temperature.

In order to measure the faster response in the post-ignition regime, an embodiment of the radiography system described above and having a pulsed x-ray source was used, as the flux from the continuous microfocus source was insufficient to allow imaging with sub-millisecond time resolution. In particular, a pulsed x-ray source with a trigger technique as described above was used to turn on the x-ray source and trigger the ultra-high speed video acquisition at the onset of the dynamic process in the HE.

Figure 15:
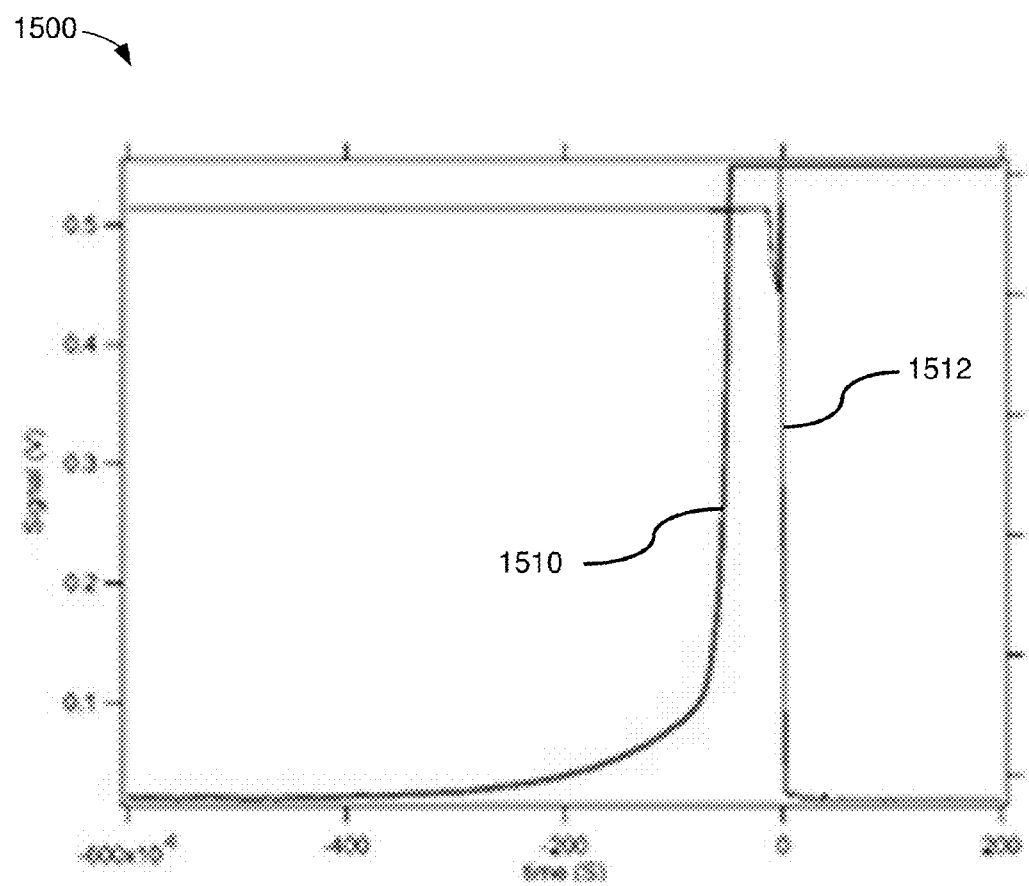
FIG. 15 is a graph showing the internal measurement of temperature used to trigger the x-ray and video acquisition in a thermal explosion experiment discussed herein.

FIG. 15 is a graph 1500 showing the voltages generated by an InGaAs photodiode, where the voltages correspond to internal measurements of temperature and can be used to trigger the x-ray and video acquisition. In particular, FIG. 15 shows an InGaAs voltage (temperature) trace as plot 1510 and breakfoil record of thermal explosion as plot 1512. In particular, the graph shows the record of an external break foil on the experiment case which serves as a time record of the case coming apart late in the thermal explosion event. Very good reproducibility has been found on the time between the steep rise in temperature and the break foil. For PBX-9501 radial thermal explosion experiments of the ½" by 1" size. The time between these two signatures is on the order of 60 microseconds.

The onset of the rapid temperature rise (time scale of microseconds) was used to trigger the pulsed x-ray source and ultra-high speed video camera. The combination of source flux and detection sensitivity enabled images with 5-7 microsecond interframe times. For PBX-9501, 7 microsecond interframe time was chosen.

Figure 16:
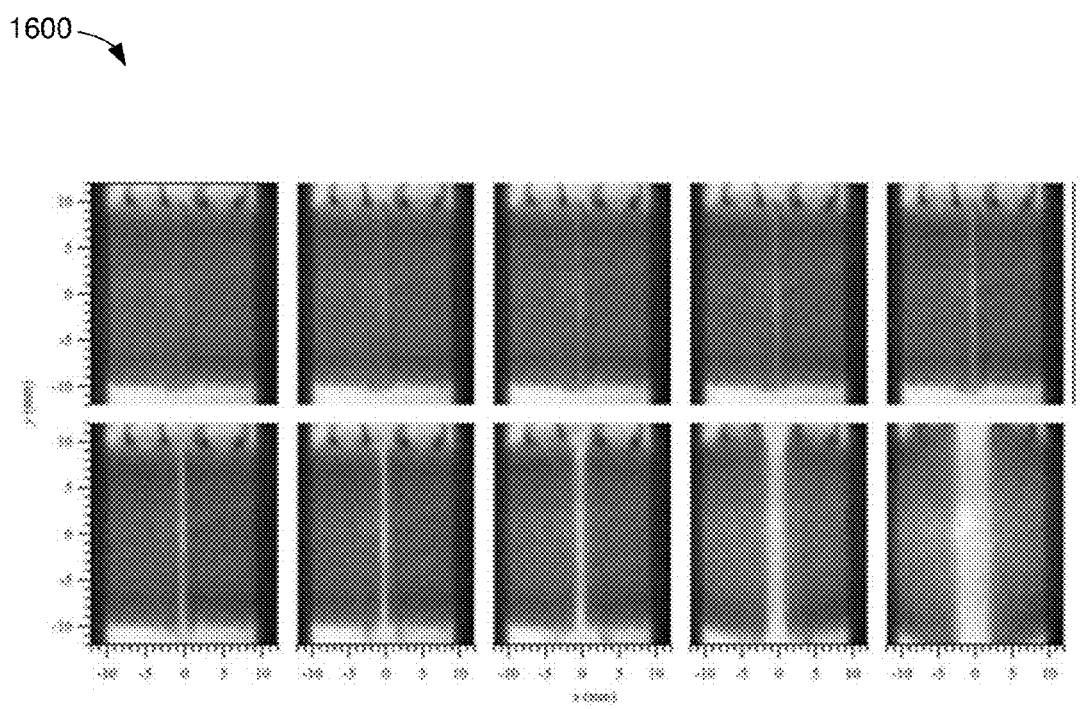
FIG. 16 shows a series of images of the direct transmission images collected during a thermal explosion experiment discussed herein.

FIG. 16 shows a series of images 1600 of the direct transmission collected with this interframe time. In particular, the series of images in FIG. 16 illustrate the convective internal burning exhibited by a sample of PBX 9501 subjected to heating until ignition at 205° C. The dynamic data are shown in direct x-ray transmission with increased transmission in the lighter regions of the image. Ignition is observed to happen near the midplane of the cylinder, with propagation to the case boundary and significant deformation at late times. Each frame was collected with a 7 microsecond interframe time. The velocity of burning in these experiments was a function of the gas phase pressure behind the burn front. The collaborative experiments described above couple internal, fiber based pressure measurements within these experiments to simultaneously measure pressure and rate of burning.

The experimental observation of observables continuously across the slow to fast timescales was enabled by using a single observable (T, ρ, or P), and acquiring the data with different time resolutions over the different regimes. The quasistatic, pre-ignition regime data was collected for thousands of seconds with second resolution. The dynamic post-ignition regime data was collected with microsecond resolution for up to seconds. Using an embodiment of the triggering technique disclosed above in which the object itself is used to trigger activation of the pulsed x-ray source, the internal temperature diagnostics were used to turn on the collection of the microsecond time scale data at a time within the time window of the thermal explosion event.

Comparing the time response for the fast observation of the different thermodynamic state variables, it can be seen that all show what is essentially a switch in response rates between the "quasistatic", or pre-ignition regime, and the dynamic, post-ignition regime. The pre-ignition observables evolve at increasing rates up to 10's of degrees per second temperature rise, and density loss in the central ignition volume over 10-20 seconds. However, on the sub-millisecond time scale, the rate of rise is essentially flat (10° C./second implies 0.01° C./mS). However, there is a sudden switch in the rate of change of all the observables in the final 100-200 microseconds leading to the thermal explosion event.

Figure 17:
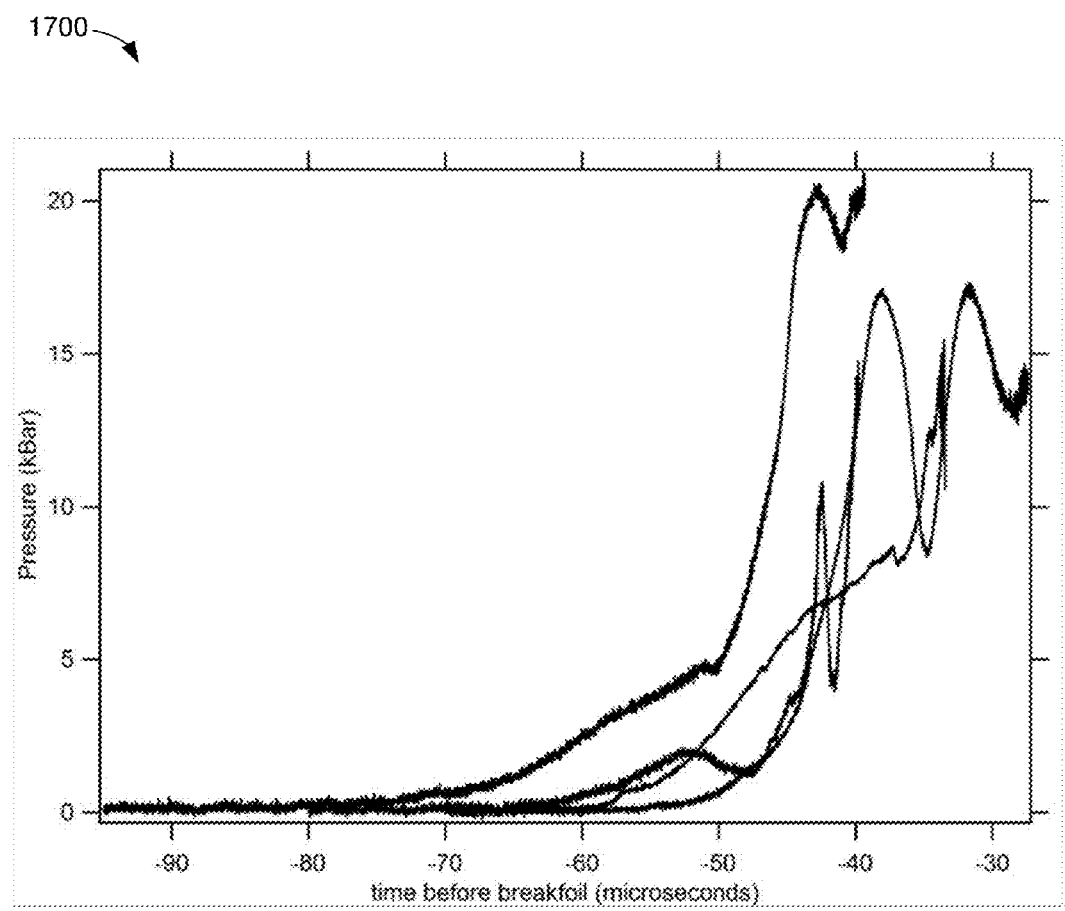
FIG. 17 is a graph that shows FBG measurement of pressure at endcap of radial thermal explosion experiments.
Figure 18:
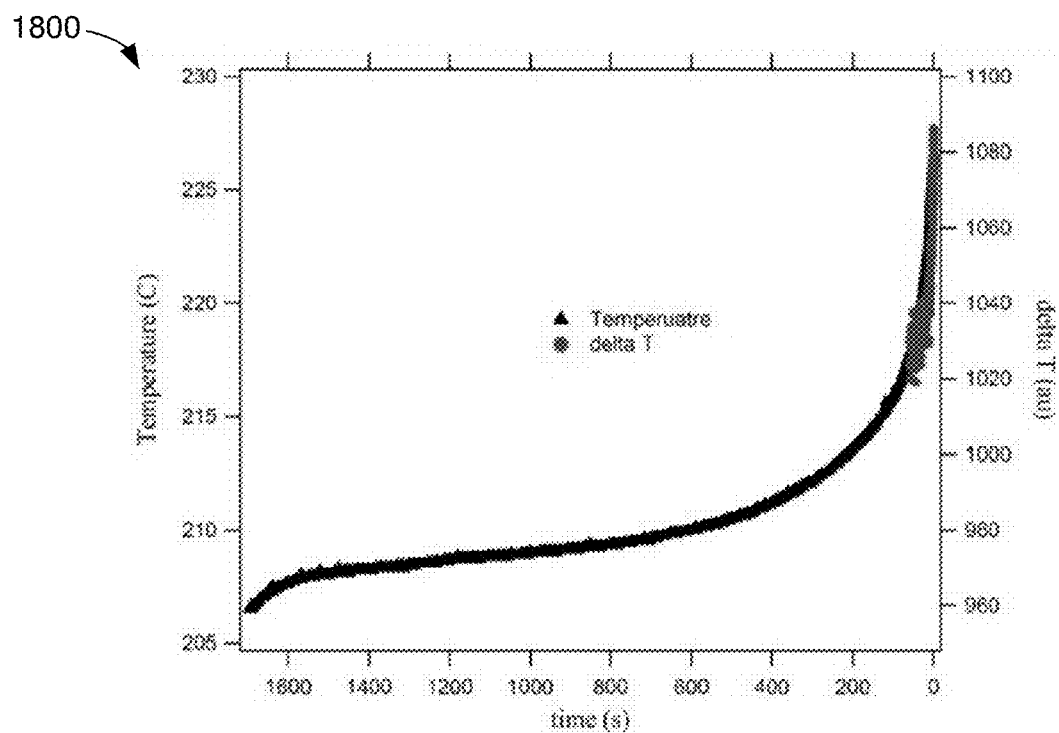
FIGS. 18 and 19 are graphs that show the comparison of temperature and density plotted linearly and logarithmically to demonstrate the switch in time scales.
Figure 19:
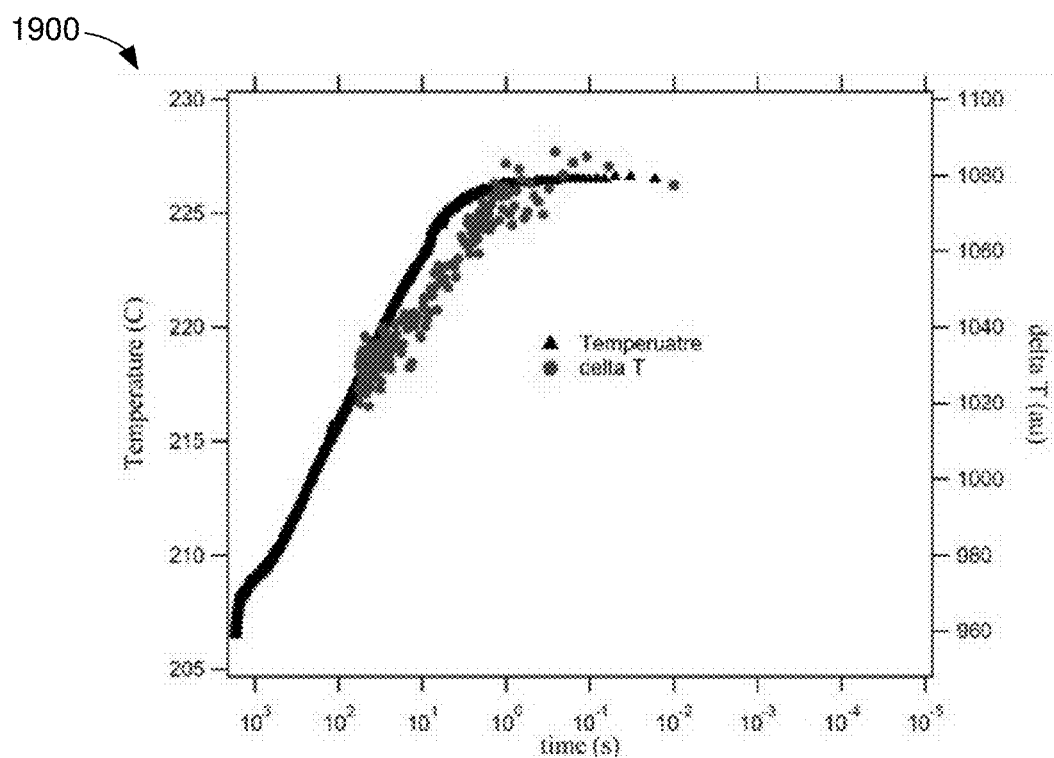
Figure 20:
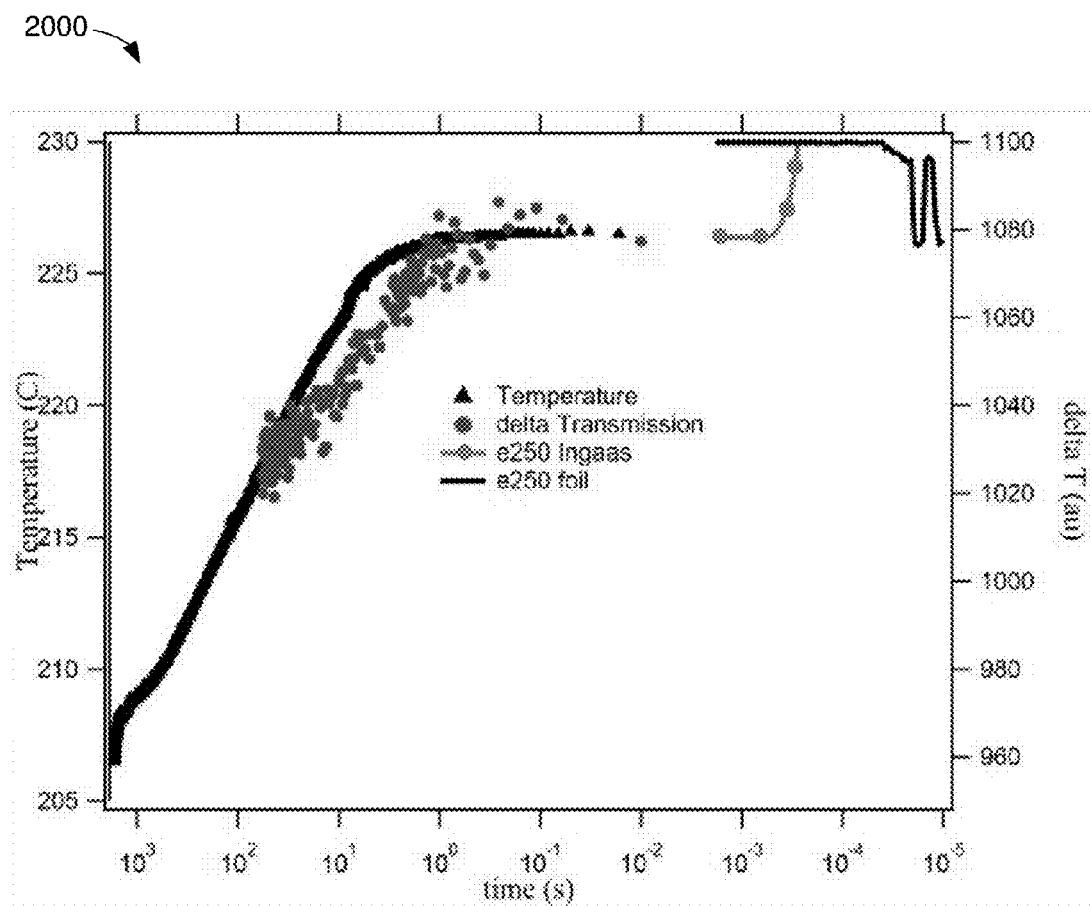
FIG. 20 is a graph that shows logarithmic time base stitching together pre- and post-ignition regimes.

FIG. 17 is a graph 1700 that shows FBG measurement of pressure at endcap of radial thermal explosion experiments. Multiple experiments are shown to show variability of the measurement. FIGS. 18 and 19 are graphs 1700 and 1800 that show the comparison of temperature and density plotted linearly and logarithmically to demonstrate the switch in time scales. In particular, FIG. 18 shows a linear time base for pre-ignition temperature and density, and FIG. 19 shows pre-ignition data on a logarithmic time axis. FIG. 20 is a graph 2000 that shows a logarithmic time base stitching together pre- and post-ignition regimes.

As discussed, the evolution of three thermodynamic state variables from the pre-ignition thermal decomposition through to the post-ignition burn propagation regime in PBX-9501 thermal explosions were followed. The temperature, density, and pressure were measured continuously across the time scales covering a duration of nearly $10^4$ seconds, with time resolutions of $10^{-6}$ seconds. All three variables show a switch in time scales in the final hundreds of microseconds leading to thermal explosion.

IV. Concluding Remarks

Having illustrated and described the principles of the disclosed technology, it will be apparent to those skilled in the art that the disclosed embodiments can be modified in arrangement and detail without departing from such principles. For example, any one or more aspects of the disclosed technology can be applied in other embodiments. In view of the many possible embodiments to which the principles of the disclosed technologies can be applied, it should be recognized that the illustrated embodiments are only preferred examples of the technology and should not be taken as limiting the scope of the invention.

What is claimed is:

1. A radiographic imaging method, comprising:
   placing an x-ray source into an armed state in which elements of the x-ray source are operative and ready for x-ray generation but no x-rays are generated; and
   triggering the x-ray source to transition into an active x-ray generation state using a signal that originates from an event occurring in an object to be imaged using the generated x-rays from the x-ray source,
   wherein the object to be imaged is a material experiencing an exothermic reaction or an explosive material and wherein the event is an onset of the exothermic reaction or an onset of an explosion of the explosive material during a period of thermal runaway experienced by the explosive material.

2. The method of claim 1, wherein the signal is produced using hardware logic components that are coupled to one or more sensors configured to detect occurrence of the event in the object.

3. The method of claim 1, further comprising triggering activation of a video capture system configured to produce x-ray transmission images of the object in response to the generated x-rays from the x-ray source, wherein the video capture system is also activated by the signal that is generated from the event occurring in the object to be imaged.

4. A radiographic imaging method, comprising:
   automatically triggering generation of x-rays and image data collection for transmission images resulting from the x-rays using one or more measurements of an object being imaged by the x-rays,
   wherein the measurements indicate a change of state in the object, and
   wherein the object is a material experiencing an exothermic reaction or an explosive material and the measurements indicate that the object has entered a state of exothermic reaction or that the object has entered a state of explosion.

5. The method of claim 4, wherein the measurements are obtained from one or more of (a) a sensor embedded into the object; (b) a sensor in contact with a surface of the object; or (c) a sensor not in contact with the object but configured to directly sense or detect a characteristic of the object.

6. The method of claim 4, wherein the generation of x-rays is performed by a gridded x-ray source, and wherein image data collection is performed by a video camera, the x-ray source and the video camera operating as part of an x-ray transmission imaging system in which x-rays interrogate the object and are detected by a scintillator, the scintillator producing light signals captured and recorded by the camera in the form of continuous video data comprising multiple consecutive frames.

7. A system, comprising:
   an x-ray source, the x-ray source comprising a gridded x-ray tube;
   a scintillator positioned to receive x-rays generated by the x-ray source;
   a video capture system configured and arranged to, when activated, capture and store image data produced by the scintillator for multiple consecutive frames; and
   an object to be x-ray imaged using the x-ray source, the scintillator, and the video capture system, the object being located between the x-ray source and the scintillator; and
   a trigger mechanism for providing a trigger signal that causes the x-ray source to begin generating x-rays,
   wherein (a) the object to be x-ray imaged is a material experiencing an exothermic reaction or an explosive material, and the trigger signal is triggered by an onset of the exothermic reaction or an onset of an explosion of the explosive material during a period of thermal runaway experienced by the explosive material; or (b) the object to be x-ray imaged is a material being strained, and the trigger signal is triggered by an onset of a material failure of the material being strained.

8. The system of claim 7, wherein the x-ray source is configured to transition from an armed state into an x-ray generation state upon receipt of the trigger signal, the armed state being a state in which a cathode and an anode of the x-ray source are active but electrons are deflected from interaction with the anode through a voltage applied to the gridded x-ray tube.

9. The system of claim 7, wherein the trigger signal causes a grid voltage in the gridded x-ray tube to change into a state that permits electrons from a cathode in the x-ray source to strike an anode in the x-ray source, thereby generating x-rays.

10. The system of claim 7, wherein the trigger mechanism comprises:
one or more sensors configured to sense a characteristic of the object to be imaged; and
one or more hardware logic components in communication with the one or more sensors and configured to generate the trigger signal when the one or more sensors produce one or more signals indicating that a trigger threshold has been reached.

11. The system of claim 10, wherein the one or more sensors include one or more of: (d) a sensor located within the object; (e) a sensor positioned in contact with a surface of the object; or (f) a sensor positioned proximate to but not in contact with the object.

12. The system of claim 10, wherein the one or more sensors include one or more of a temperature sensor, light sensor, strain sensor, pressure sensor, or sound sensor.

13. A radiographic imaging method, comprising:
placing an x-ray source into an armed state in which elements of the x-ray source are operative and ready for x-ray generation but no x-rays are generated; and
triggering the x-ray source to transition into an active x-ray generation state using a signal that originates from an event occurring in an object to be imaged using the generated x-rays from the x-ray source,
wherein the object to be imaged is a material being strained and wherein the event is an onset of a material failure of the material being strained.

14. The method of claim 13, wherein the signal is produced using hardware logic components that are coupled to one or more sensors configured to detect occurrence of the event in the object.

15. The method of claim 13, further comprising triggering activation of a video capture system configured to produce x-ray transmission images of the object in response to the generated x-rays from the x-ray source, wherein the video capture system is also activated by the signal that is generated from the event occurring in the object to be imaged.

16. A radiographic imaging method, comprising:
automatically triggering generation of x-rays and image data collection for transmission images resulting from the x-rays using one or more measurements of an object being imaged by the x-rays,
wherein the measurements indicate a change of state in the object, and
wherein the object is a material being strained and the measurements indicate that the object has entered a state of material failure.

17. The method of claim 16, wherein the measurements are obtained from one or more of (g) a sensor embedded into the object; (h) a sensor in contact with a surface of the object; or (i) a sensor not in contact with the object but configured to directly sense or detect a characteristic of the object.

18. The method of claim 16, wherein the generation of x-rays is performed by a gridded x-ray source, and wherein image data collection is performed by a video camera, the x-ray source and the video camera operating as part of an x-ray transmission imaging system in which x-rays interrogate the object and are detected by a scintillator, the scintillator producing light signals captured and recorded by the camera in the form of continuous video data comprising multiple consecutive frames.

* * * * *